Figure 1:
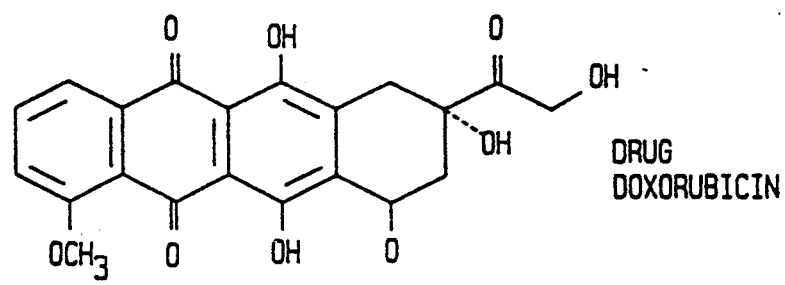
Figure 1:
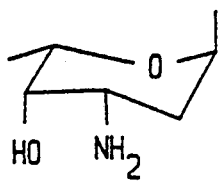
Figure 1:
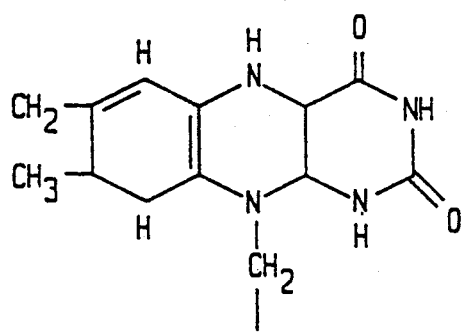
Figure 1:
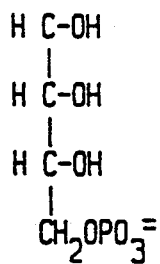

United States Patent [19]

Morgan, Jr. et al.

[11] Patent Number: 5,106,951
[45] Date of Patent: Apr. 21, 1992

[54] ANTIBODY CONJUGATES

[75] Inventors: Alton C. Morgan, Jr., Edmonds; Ananthachari Srinivasan, Kirkland; John M. Reno, Brier; Alan R. Fritzberg, Edmonds; David C. Anderson, Seattle, all of Wash.

[73] Assignee: NeoRx Corporation, Seattle, Wash.

[21] Appl. No.: 332,610

[22] Filed: Mar. 31, 1989

Related U.S. Application Data

[63] Continuation-in-part of Ser. No. 157,895, Feb. 19, 1988, abandoned.

[30] Foreign Application Priority Data

Feb. 17, 1989 [EP] European Pat. Off. ........ 89102809.4

[51] Int. Cl.$^5$ .............................................. C07K 17/00
[52] U.S. Cl. ................................. 530/391.9; 530/402; 530/403; 530/404; 530/405; 530/391.7
[58] Field of Search ................ 530/403, 403, 404, 405, 530/391

[56] References Cited

U.S. PATENT DOCUMENTS

| | | | |
|---|---|---|---|
| 3,867,423 | 2/1975 | Crabbe | 260/468 |
| 4,472,500 | 9/1984 | Milstein et al. | 435/68 |
| 4,474,893 | 10/1984 | Reading | 436/547 |
| 4,507,234 | 3/1985 | Kato et al. | 260/121 |
| 4,534,971 | 8/1985 | Fisher | 514/21 |
| 4,642,335 | 2/1987 | Miyashiro et al. | 530/409 |
| 4,671,958 | 6/1987 | Rodwell et al. | 424/86 |
| 4,689,311 | 8/1987 | Weltman | 436/519 |
| 4,698,420 | 10/1987 | Urnovitz | 530/387 |

FOREIGN PATENT DOCUMENTS 0279862 8/1988 European Pat. Off. .
2312259 12/1976 France .

OTHER PUBLICATIONS

Hamilton et al., J. Am. Chem. Soc., vol. 109, pp. 5035-5036 (1987).
Chang et al., J. Am. Chem. Soc., vol. 110, pp. 1318-1319 (1988).
Hamilton et al., J. Am. Chem. Soc., vol. 108, pp. 5158-5167 (1986).
Hamilton et al., Tetrahed. Lett., vol. 26, pp. 5735-5738 (1985).
Mann et al., J. Chem. Soc. Chem. Commun., vol. 2, pp. 158-160 (1986).
Hamilton et al., J. Chem. Soc., Chem. Commun., vol. 5, pp. 311-313 (1984).
Rebek et al., J. Am. Chem. Soc., vol. 109, pp. 5033-5035 (1987).
Rebek, Science, vol. 235, pp. 1478-1484 (1987).
Dalmarle et al., Molecular Pharmacology, vol. 22, pp. 158-165 (1982).
Pant et al., J. Am. Chem. Soc., vol. 110, pp. 2002-2003 (1988).
Pant et al., J. Incl. Phen., vol. 5, pp. 109-111 (1987).
Larkins et al., Tetrahed. Lett., vol. 27, pp. 2721-2724 (1986).
Kelly et al., Int. J. Peptide Protein Res. 26:400-406 (1985), "DNA-Binding Compounds-Synthesis and Intercalating Properties of a Peptide-Diamino Diacridine".

Primary Examiner—F. T. Moezie
Assistant Examiner—Andrew G. Rozycki
Attorney, Agent, or Firm—Seed and Berry

[57] ABSTRACT

There is disclosed an antibody and antibody-drug conjugate for targeting drug delivery as well as a class of chemicals, termed a drug-binding molecule of complementary structure (csDBM). The csDBM is designed to "fit" the drug by combining multiple non-covalent interactions between functional groups on the drug and opposing functional groups on the csDBM. The net result on the antibody-csDBM-drug conjugate is a drug stably bound to the csDBM so as not to dissociate during in vivo administration, but not so tightly bound to allow drug dissociation from the conjugate without significant loss of activity and retaining the drug's ability to bind to a higher affinity site on or within the target cell.

12 Claims, 3 Drawing Sheets

DRUG
DOXORUBICIN

FLAVIN MONONUCLEOTIDE
(REDUCED)

ANTIBODY CONJUGATES

RELATED APPLICATIONS

This application is a continuation-in-part of U.S. application Ser. No. 157,895, filed Feb. 19, 1988, which application is now abandoned.

TECHNICAL FIELD

The present invention relates to compounds which function to bind drug molecules non-covalently to a carrier or antibody with such affinity that there is little dissociation of the drug from a carrier or antibody and with no loss of drug potency, but with a reduction in toxicity. The compounds can be used to conjugate a drug to a delivery system, such as an antibody or other targeting protein. The drug-binding molecules can occur in nature or can be designed to bind specifically to a drug by using compounds with similar structures but with one or more "opposing" functional groups, capable of forming non-covalent bonds, opposite each drug functional group and thereby complexing with the drug via multiple non-covalent interactions.

BACKGROUND OF THE INVENTION

There has been considerable interest in the "magic bullet" approach to cancer therapeutics. Recent efforts have been devoted to the conjugation of chemotherapeutic neoplastic drugs to specific antibodies, such as monoclonal antibodies, to produce conjugates which can selectively target tumor cells while sparing normal tissues. Different classes of agents have been considered for this application. These include beta- and alpha-emitting isotopes, plant and bacterial toxins, and a variety of antineoplastic drugs, including intercalating agents, antimetabolites, alkylating agents, and antibiotics. It is desirable to conjugate chemotherapeutic drugs to antibodies for the following reasons:

1. It has recently been shown that up to 1,000-fold more drug can be delivered to tumor cells when conjugated to an antigen-specific monoclonal antibody than is possible by the addition of free drug.

2. Pleiotropic drug resistance may arise following treatment with one of a number of chemotherapeutic drugs, resulting in inducing resistance to drugs of several classes. The mechanism(s) of this resistance are not entirely known, but it is known that this resistance can be partially overcome by antibody targeting of drugs.

3. Even though current chemotherapeutic drugs are active against only some of the major tumor types, the response rate in drug-insensitive tumor types may be increased by antibody-mediated delivery.

4. Many dose-limiting toxicities, which are now seen with chemotherapeutic drugs, may be reduced by conjugation to an antibody. A decrease in toxicity with at least equal efficacy would give a superior product, and the product would have a higher therapeutic index.

To create conjugate with a drug and an antibody, the drug may be directly linked to the antibody through nucleophilic substitution of certain groups on the antibody (e.g., lysines, carboxyl, or sulfhydryl), or the drug may be conjugated to the antibody via hetero- or homobifunctional cross-linkers. Linker groups may be small organic compounds or peptides substituted with chemical linkers for conjugation. Large carriers have also been used containing linker groups and offer the advantage of being able to bind many drug molecules to a single antibody. Examples of carriers are the polymers of lysine and glutamic acid, dextran, and the polypeptide albumin.

Drugs have been thus far conjugated to antibodies or carriers only by using covalent bonds. See Biair and Ghose, *J. Immunol. Meth.* 59:129–144, 1983. Covalent bonds can be further subclassified into non-metabolizable and metabolizable bonds. Metabolizable bonds are those that undergo hydrolysis, releasing the drug under conditions present within or around cells, such as low pH, a reducing environment, or through proteolysis. An example of metabolizable covalent bonds which are useful are those that are sensitive to the low pH environment of endosomes within a cell. See Shen and Ryser, *Biochem. + Biophys. Res. Commun.* 102: 1048–1054, 1981. After the drug-antibody conjugate binds to the cell, it may be internalized by a pathway that places it in an endosome where the conjugate is subjected to a low pH environment. The hydrolysis of the conjugate's covalent bond releases free drug, where it may then exert its cytotoxic activity.

A non-metabolizable bond can also result in active drug conjugates. However, the resulting conjugates with non-metabolizable bonds generally have reduced drug potency as compared with those conjugates formed with metabolizable bonds. This is because intracellular processing via proteolysis does not release the drug as efficiently as metabolizable bonds. In addition, the drug, if released, is usually in a form different from the native drug and has reduced cytotoxic potency.

Covalent drug-antibody conjugates have been made where the drug is conjugated directly to the antibody and also where the drug is covalently bound to a carrier before conjugation to the antibody. See U.S. Pat. No. 4,507,234, Garnett and Baldwin, *Cancer Res.* 46: 2407–2412, 1986. Direct conjugation consists of a drug's being conjugated to residues within the antibody molecule, including, for example, lysine and glutamic acid amino groups, sulfhydryl groups and sugar residues within oligosaccharide chains. An important limitation of this direct conjugation approach is that the antibody may be exposed to harsh conjugation conditions, that may denature the antibody causing more rapid clearance from the serum after injection. Unless the direct conjugation is site directed (e.g., at the carbohydrate or sulfhydryl groups), the immunoreactivity of the conjugate may be compromised. Even when combined with site-direction, direct conjugation can still result in non-selectivity (i.e., kill antigen-positive and antigen-negative cells with approximately equal potency) and poor target localization, due to the nature of the agent conjugated to the antibody. As an example, ricin A chain conjugated via site-directed sulfhydryl groups to antibodies is rapidly taken up by liver phagocytes due to mannose receptors for carbohydrate on the ricin A chain. This can also occur with highly lipophilic drugs because lipophilic drugs in free drug form must have some means for interacting with cells to be effective. One such mechanism for lipophilic drugs is insertion into the cell membrane lipid bilayer. If the direct drug-antibody conjugate is formed with a metabolizable covalent bond, this bond can often be metabolized at other sites within the body, such as within the blood, liver, spleen, and other organs.

The indirect method of conjugation first requires the coupling of a drug to a carrier, generally via a linker group. The carrier is then conjugated to the antibody, via a heterobifunctional linker, that can be first conjugated to the carrier and then activated following drug conjugation. One advantage of this indirect conjugation route is that large numbers of drug molecules may be linked to an antibody for delivery to the target site. However, large numbers of drug molecules linked to an antibody may also lead to enhanced nonspecific uptake due, for example, to the lipophilicity of the drug. The indirect conjugation approach does not expose the antibody to the harsh conditions of conjugation, as the chemical manipulations are usually performed on the carrier and not the antibody. Furthermore, the carrier can enhance the solubility of the drug conjugate.

Direct or indirect conjugation of a drug to an antibody creates a stable conjugate that can arrive at the target site with a minimum of dissociation of the drug. One needs, however, to couple this property with a mechanism of selective release of drug for maximal potency.

Selective release may be exploited at three levels. The first is intracellular release within the tumor cell. The best examples of this form of release are pH-sensitive and reducible bonds which, upon intracellular processing of the conjugate, break down to release free drug. This requires binding and internalization of the conjugate prior to drug dissociation. Intracellular internalization of the conjugate requires that the conjugate either enter the cytoplasm or be taken up into an endosome, or lysosome. Internalization rates with monoclonal antibodies to antigens of solid tumors is slow. Thus, a drug conjugate requiring such a process for release of active drug will not be highly potent. In addition, not all internalized conjugate undergoes appropriate intracellular processing for release of active drug. Conjugates that are processed into lysosomes are probably degraded and some drugs will be inactivated. Conjugates processed in the endosomes or into the cytoplasm have the opportunity to release their drugs and allow drugs access to the intracellular target.

A second site for the selective release of drug from the conjugate is the plasma membrane. One example of the plasma membrane release mechanism is referred to in U.S. Pat. No. 4,671,958. In this case, conjugate that is once bound to tumor cells activates complement, which causes the proteolytic degradation of sensitive peptide linkages, to which the drug is bound and releases it in free form.

A third level for drug release would be at the tumor site, but before the conjugate is bound to the tumor cell. This third form of release requires a drug-antibody linkage that would take advantage of certain differences between tumor and normal tissue extracellular milieu. None have been developed to date.

Covalent drug conjugates discussed above comprising cytotoxic or antineoplastic drugs covalently conjugated to an antibody with or without the use of a carrier through linker groups, in a site- or non-site-directed manner, suffer from a number of problems. First, covalent conjugation of drug to antibody requires derivatization of the drug to produce a form of the drug capable of being conjugated to groups in the antibody or carrier. This typically results in a reduction of the drug's cytotoxic activity or potency, due to chemical modification of its functional groups. For some drugs, exposure to the conditions for derivatization may be sufficient to inactivate the drug. For others, the derivatization is not well enough controlled so that groups important for the drug's cytotoxic activity are chemically modified, although these groups are not the primary targets of the procedure. The use of labile bonds, such as pH- sensitive bonds, may overcome part of this problem, but may still result in relatively slow release of the drug at the targeted site or release of the drug in a modified, less active form.

Extracellular release of the drug from the conjugate, as described in U.S. Pat. No. 4,671,958, overcomes the internalization and intracellular processing problems associated with conjugates. The drug, however, still must be derivatized appropriately in order for it to be covalently bound to carbohydrate residues within the antibody molecule, either directly or through a carrier-mediated system. In addition, the rates of release of the drug will be governed by the half-life of the antibody on the plasma membrane of the tumor cells and by the rate of complement fixation of the antibody. This process is a handicap with most murine monoclonal antibodies (the type most often used), that have little or no ability to fix human complement.

The current generation of immunoconjugates of drugs and antibodies suffer from the additional problem of poor selectivity. This problem of decreased selectivity can be assessed by testing drug conjugates in vitro against antigen-positive and antigen-negative cells. Antigen-positive cells are usually killed at drug-conjugate concentrations tenfold or less lower than antigen-negative cells. This is true, for example, for anthracycline conjugates. Conjugates of the same antibody and a plant or bacterial toxin will, by contrast, typically show 3 to 4 logs of selectivity. It thus seems apparent that the cytotoxic drug itself has additional mechanisms for interacting with cell membranes, and that this leads to nonselective cytotoxicity. Moreover, there is often more than one drug molecule conjugated to an antibody molecule with each drug molecule being capable of nonselective cellular interactions. Thus, there is a considerable need in the art to improve the selectivity of drug immunoconjugates. This can provide improved delivery in vivo to tumor sites as well as decreased normal tissue uptake.

SUMMARY OF THE INVENTION

The above-identified problems can be addressed and the current generation of immunoconjugates improved by the use of non-covalent binding methodologies for conjugating drugs to antibodies or to other carrier molecules. The use of non-covalent binding does not expose the drugs to harsh derivatization conditions and thereby does not compromise the potency of the drug. The use of non-covalent binding methodologies produces sufficiently high affinity of binding of the drug for targeting, but also sufficiently labile binding so that the cytotoxic drug may transfer at the target site to drug acceptors on the cell surface or within the tumor cell. Indeed, one of the advantages of the non-covalent approach is that it allows discrete titration of the affinity of interaction to produce the desired balance of drug binding and release. The conjugate envisioned by the present invention comprises a carrier-drug or targeting protein conjugate for slow drug release or targeting drug delivery, respectively. Such conjugates comprise a targeting protein such as an antibody or antibody fragment, or carrier molecule; a moiety termed a drug-binding molecule of complementary structure (abbreviated csDBM and described further below) which is covalently bound to the antibody or carrier; and a drug non-covalently complexed to the csDBM. In a separate configuration, drug can be first bound through covalent bonds to antibody or carrier and then complexed with a csDBM to improve the cytotoxic selectivity of the killing. The csDBM can be found in nature and modified as necessary or specifically designed.

Non-covalent association of a drug with a carrier protein or antibody is random and heterogenous in binding affinities, and generally results in only low levels of bound drug. The less stably bound drug is considered undesirable due to the increased potential for premature release and increased risk of host toxicity and a reduced ability to localize to tumor sites. The present invention provides for a csDBM that is specifically designed to fit the drug molecule and undergo multiple non-covalent interactions with a drug to enhance its binding affinity to antibody or a carrier and to provide a conjugate stable enough to arrive at target sites with most of the drug still bound.

This invention also comprises a soluble complex of drug and a csDBM. This preformed complex is administered as a pharmaceutical material to decrease the toxicity of a cytotoxic regimen or to provide a mechanism for the slow release of free drug. The csDBM alone may also be injected at the local site of drug injection to prevent toxicity, such as the extravasation of doxorubicin around an intravenous site of injection.

BRIEF DESCRIPTION OF THE DRAWINGS

FIG. 1 depicts a doxorubicin molecule and a naturally occurring csDBM, flavin mononucleotide (reduced). The alignment of the two molecules (when superimposed on one another) indicates the pi-pi bonding or stacking which the two molecules can undergo. Potential hydrogen bonds of this drug/antimer complex are also expected to form. In addition, ionic binding can occur between the amino group of the drug and the phosphate groups of the csDBM. The multiple noncovalent interaction results in a high affinity complex. The csDBM can be modified with typical nucleophilic groups like active esters or malimides, for conjugation to antibody or carrier.

FIG. 2 compares the potency and selectivity of covalent and noncovalent antibody (NrML-5)/csDBM (FAD)/drug (Dox for Doxorubicin or adriamycin conjugates). The assay reported in FIG. 2 is an in vitro cytotoxicity assay for both antigen positive melanoma cells (top) and antigen negative melanoma cells (bottom). The monoclonal antibody NrML-5 is specific for the melanoma antigen. The bar graphs show percentage survival as determined by MTT dye uptake and metabolism (Example 5).

FIG. 3*a* depicts a best-fit titration curve for 50 $\mu$M doxorubicin and varying concentrations of the peptide DK(Fmoc)GK(Fmoc)DGGC-amide in $\mu$M.

FIG. 3*b* shows the binding at absorbance wavelengths of 565 nm and 580 nm, for a best-fit dissociation constant at 48 $\mu$M peptide concentration.

DETAILED DESCRIPTION OF THE INVENTION

Prior to setting forth the invention, it is helpful to set forth certain definitions.

csDBM

The term "csDBM" is not presently used in the art but is introduced here to describe the present invention. The term "csDBM" is an abbreviation for "drug-binding molecule of complementary structure," and refers to a molecule that has a form opposite and complementary to that of a drug, wherein the csDBM will bind the drug through non-covalent interactions. In this patent application, the term csDBM is used to mean a molecule having functionalities that are opposite and complementary in structure to a drug molecule. Preferably, the csDBM and drug will have similar planar ring structures, but with opposing functionalities. Opposing functionalities on the csDBM will include groups for hydrogen and ionic binding and other non-covalent interactions, with or without electron poor (e.g., groups giving rise to acidic protons) or electron rich (e.g., unshared electron pairs on heteroatoms and anionic groups, such as carboxylates) groups on the csDBM to increase the pi binding. Furthermore, the opposing functional groups on the csDBM will be sterically oriented in proper three-dimensional alignment such that the functional group on the drug can interact with the opposing functional group on the csDBM in proper steric orientation.

Functional Group

Functional group is that part of a molecule that can interact and form an association or bond with another group. For example, electron-rich groups, electron-poor groups, dipoles with hydrogen bonding potential, as well as ionic moieties, are examples of functional groups. Referring to the structure of doxorubicin in FIG. 1, the keto group, the hydroxy group, the methoxy group, and the amino group are examples of functional groups on the doxorubicin molecule.

Antineoplastic Agent

An antineoplastic agent is a drug molecule that has cytotoxic activity by virtue of its ability to inhibit DNA, RNA, protein synthesis, or some other essential cellular function, ultimately leading to cell death.

Non-Covalent Bond

A non-covalent bond is defined as an ionic bond, a hydrogen bond, a pi-pi bond, hydrophobic interactions and van der Waals interactions.

Covalent Bond

A covalent bond is defined as the formation of a sigma bond between two organic molecules.

Electron-Rich Groups

An electron-rich group contains excess electrons or available basic non-bonding pairs of electrons. Examples of electronrich groups include but are not limited to carboxylates, sulfonates, phenoxides, and groups containing heteroatoms with unshared pairs of electrons, such as oxygen, sulfur, and nitrogen.

Electron-Poor Groups

An electron-poor group is electron deficient as in cations or containing atoms of high electronegativity. Electron-poor groups include but are not limited to protons bound to heteroatoms thereby being acidic, ammonium nitrogen atoms, and nitro groups.

Steric Location

The steric location of a functional group on a csDBM is that position where the opposing functional group should be located on the csDBM to line up opposite the drug's functional group and allow for a noncovalent bond to form between the drug's functional group and the csDBM's opposing functional group.

Carrier

A carrier is a polypeptide, polymer, or protein such as poly-1-lysine, poly-1-glutamate, polymeric dextran, or albumin. A carrier is used to bind drug to antibody or targeting protein to increase the loading without reducing immunoreactivity of the antibody.

Targeting Protein

A targeting protein comprises any protein moiety that can specifically bind to a target cell or target site. Examples of targeting proteins include antibodies, antibody fragments (Fab, F(ab')$_2$, and Fab'), monoclonal antibodies, monoclonal antibody fragments and peptide hormones that can bind to specific cellular receptors. The targeting protein serves to direct the complex or conjugate to a specific target site or a specific group of target cells.

Linker Group

A small peptide or organic molecule with hetero- or homo-bifunctional linkages for conjugation of drug to a carrier or antibody.

Complementary Groups

Functional groups capable of interacting with each other to produce attraction forces between two molecules. An electron-poor and an electron-rich group is an example of complementary groups.

Briefly stated, the present invention is a csDBM, a csDBM/drug complex, a carrier/csDBM/drug conjugate, a targeting protein/csDBM/drug conjugate, a targeting protein/carrier/csDBM/drug conjugate, a targeting protein/drug/csDBM complex, a targeting protein/carrier/drug/csDBM complex and a method of designing or producing a csDBM wherein a csDBM can be identified in nature or synthesized that will undergo multiple, non-covalent interactions with a drug. Though each interaction is relatively weak on its own, when combined, they produce a strong bond to the drug. The non-covalent binding of the csDBM to drugs is, in many ways, analogous to drug-receptor site interactions, that combine hydrophobic, ionic and hydrogen binding to produce stable and selective binding of a drug to its receptor. The csDBM uses concerted, multiple, non-covalent interactions to produce stable complexes or conjugates of drugs. The stable complex of drug non-covalently bound to a csDBM is, in turn, covalently bound to a targeting protein. This is accomplished by first producing a molecule that is a csDBM, i.e., similar in structure but having opposing and complementary functionalities, to the drug that is to be conjugated. The opposing and complementary functionalities of the csDBM are sterically oriented on the csDBM molecule to orient to the functionalities of the drug. This usually results in a similar spatial configuration of the structures of the drug and the csDBM.

Preferably, the csDBM and the drug will have a planar ring structure as nearly identical to each other as possible. This will allow for "stacking" and pi-pi or charge-transfer interactions. These interactions alone are insufficient to produce high-affinity binding, and thus opposing complementary functional groups are situated around the planar ring to interact via hydrogen or ionic bonding with functional groups of the drug. Similarly, in addition, if electron-rich groups are present on the drug, electron-poor groups can be situated on the planar ring of the csDBM so as to enhance the pi-pi or stacking between drug and csDBM.

One form of a non-covalent bond is a hydrophobic (pi-pi) bond formed between ring structures. Preferably, the ring structures have a similar configuration. Planar ring structures are examples of similar configurations. Hydrogen bonding can occur between a negative dipole, such as $-C=0$, and a positive dipole, such as OH. Hydrogen bonding is formed between groups with heteroatoms containing basic unshared pairs of electrons, such as oxygen as in $C=0$ carbonyl, and groups with cations, such as substituted amines and acidic protons on heteroatoms. Ionic, non-covalent bonds are formed between anionic groups, such as phosphates, phosphonates, sulfonates and other groups with strongly acidic hydrogen atoms and cationic groups, such as $NH^+_3$. This list is not meant to be limiting as functionalities may vary in their ability to undergo non-covalent interactions with a drug because of the context of ring structures on which the functionality is found.

Often, drugs such as doxorubicin cause extravasation or local necrosis as a form of toxicity at the site of injection. The simultaneous or following administration of a csDBM to doxorubicin will to allow binding of the csDBM to the free drug at the local injection site and function to reduce local extravasation of free drug. Similarly, other locally necrotic drugs can have local toxicity reduced by administration of the csDBM.

In designing a csDBM to bind non-covalently to a specific drug, the overall affinity of the drug for the csDBM structure can be adjusted by increasing or decreasing the number of possible non-covalent interactions between drug and csDBM. Generally, the binding has to be approximately $\geq 10^6$ moles/liter in order for the drug/csDBM to be sufficiently stable for in vivo delivery, yet the affinity must be low enough for ultimate transfer of the drug to target acceptor sites. The number of groups on the csDBM that can undergo non-covalent interactions can be modified by organic synthesis of rings with different numbers of groups or by simple oxidation or reduction of existing csDBMs. An example is that of flavin adenine dinucleotide, a natural csDBM to doxorubicin, which has the potential for three hydrogen bonds per flavin ring in its reduced state but only one hydrogen bond in its oxidized state.

For conjugation, FAD is modified at the indicated R group (see examples). Drug-binding molecules of complementary structure for other drugs are shown in Examples 9-14. In addition, the FAD csDBM can be used to bind other known chemotherapeutic drugs with similar ring structures to doxorubicin. Examples include the anthracycline derivatives morpholino and cyano morpholino doxorubicin, epirubicin, actinomycin D, ellipticine and mitomycin-C.

The initial non-covalent interaction of the drug and csDBM can, if necessary, be enhanced by preforming the drug/csDBM complexation in the presence of a dehydrating agent. Water molecules will interfere with pi-pi and hydrophobic interactions. Thus, removal of water initially enhances these binding interactions. Once formed, the complexes are more resistant to rehydration. Table 1 below lists useful dehydrating agents for promoting drug-csDBM interactions and a corresponding concentration range in percentage v/v for optimal interaction of the drug and csDBM.

TABLE 1

| Dehydrating Agent | Concentration Range |
| --- | --- |
| Glycerol | 0.5 to 30 |
| Polyethylene Glycol | 0.5 to 10 |
| Ethylene Glycol | 0.5 to 50 |
| Sodium Sulfate | 0.5 to 18 |
| Ammonium Sulfate | 0.5 to 50 |

The present invention also envisions the concept of amplification using csDBMs. Amplification is achieved when an antibody molecule is complexed with a csDBM and a drug is then complexed to the conjugated csDBM. The drug complexed to the conjugated csDBM can still interact with a second csDBM molecule, and form an equilibrium complex between the three molecules. A second layer of csDBM can be added, followed by a second layer of drug. The process can be repeated until the solubility of conjugate is compromised. This stacking process, i.e., amplification, allows for multiple drug molecules to be carried with a low level of derivatization of antibody.

Another method of constructing conjugates of the csDBM is to complex drug covalently bound to antibody, either directly or through a carrier, in order to interfere with the drug's normal interactions with cells. Any one of a number of drugs may be conjugated to antibody (e.g., anthracyclines). The csDBM is dialyzed into the mixture after drug conjugation. In this situation, the csDBM serves to "shield" the drug from the cell and only permits the antigen antibody interaction to direct the targeting of the conjugate. The csDBMs may be selected by complexation with a drug and then tested for retention of potency. Different csDBMs with different affinities for the drug will reduce in vitro potency to different degrees, as shown in Example 8 of this application.

The conjugates and complexes of the present invention can be administered in vivo in any suitable manner, such as intravenously, subcutaneously, intralymphatically, intraperitoneally, intramuscularly, directly into the target tissue or even orally. The conjugates or complexes administered by injection are in the form of compositions comprising the inventive conjugate or complex plus pharmaceutical excipients that are known in the art for pharmaceutical formulations.

The "post-form" approach to building a drug-csDBM-antibody conjugate is a two-step method. First, the csDBM is covalently bound to the antibody. Subsequently, the drug is non-covalently bound to the csDBM. For binding of the drug, not all the functional groups on the csDBM need be used. Thus, some will be available, like COOH groups for substitution for conjugation. Nucleophilic groups useful for conjugation are, for example, activated esters or maleimides. A csDBM also encompasses compositions of a targeting protein or carrier substituted with molecules that are partial csDBMs but when situated adjacent to endogenous groups on proteins, can create a full csDBM structure.

Examples of two partial csDBMs are cardiolipin and adenosine triphosphate. Each contains at least two adjacent phosphate groups that can undergo strong ionic binding with doxorubicin. When such "partial csDBMs" are conjugated to antibody, or carrier, in juxtaposition to aromatic amino acids, these latter groups provide further pi or hydrogen binding and thus complete the csDBM structure. Theoretically, the juxtaposition of aromatic residues with the partial csDBMs is not as easily controlled as the conjugation of the complete csDBM structure.

Under certain conditions, an appropriate juxtaposition of aromatic as well as charged amino acid residues may occur in an antibody or carrier protein like albumin, that may form a csDBM structure capable of binding, such that only the dehydrating agent need be used to initiate the reaction. However, drugs with such a high degree of interaction with a protein are uncommon. This latter example is analogous to albumin binding of drugs. Typically, drugs have both high- and low-affinity sites within albumin. The high-affinity sites require juxtaposition of charged and aromatic amino acid residues. This indicates that albumin may be particularly useful as it already satifies some of the interactions necessary for drug binding. Since this is well known in the art, what is envisioned is the use of agents as in Table 1, to promote drug/protein interactions, and the application of non-covalently bound drug/protein complexes to target delivery is a part of this invention.

In one embodiment of the invention, an aromatic drug is non-covalently bound to (e.g., intercalated between) two or more aromatic groups on an oligopeptide or analog thereof. The aromatic groups may be the same or different and generally are side chains on the "backbone" of the peptide or peptide analog (e.g., a hydrocarbon chain, which may be substituted with oxygen, nitrogen or other heteroatoms). The resulting complex generally exhibits more stable drug binding than the above-described csDBM complexes in which a drug is bound through interactions with only one planar ring structure. This drug carrier system should be useful for aromatic drugs used in treating a variety of diseases, including cancer.

One example of this embodiment of the invention involves oligopeptide sequences comprising two or more amino acids with aromatic side chains. By "aromatic side chains" is meant a side chain comprising at least one aromatic ring. The aromatic side chains are spaced to permit binding of an aromatic drug through interactions (including intercalation) with two of the side chains. A targeting protein may be engineered to contain the desired oligopeptide, using known protein engineering or recombinant DNA techniques. Alternatively, an oligo-peptide may be attached to a targeting protein (e.g., using a cross-linking reagent), preferably after drug binding. The resulting conjugates are useful for delivering the drug to a desired target site in vivo.

The oligopeptide may be synthesized, using known peptide synthesis techniques, and may include both natural and the so-called "unnatural" amino acids. The oligopeptides are designed to non-covalently bind the drugs by intercalation of the drug between aromatic side chains of the synthetic peptide or by other interactions of the drug with the peptide side chains. Charged side chains may be included elsewhere in the oligopeptide to make the entire complex more water soluble, and perhaps assist in drug binding. The amino acids in the peptide sequence may be chosen to manipulate the charge density and secondary structure to overcome severe solubility problems plaguing earlier efforts to attach aromatic drugs to antibodies. Including repeating units of a drug intercalating or binding sequence allows the oligopeptide to bind multiple drug molecules, thereby loading the targeting protein with multiple drug molecules for enhanced therapeutic efficacy.

The type and position of side chains in the oligopeptide are chosen according to the structure of the drug to be bound. The drug may be any drug that contains at least one aromatic ring, such as one of the above-described aromatic drugs, including those presented in the examples below. The side chains on the peptide backbone should have at least one planar ring structure that is similar to a ring in the drug to be bound. If the drug contains multiple rings, the side chains preferably also comprise similar multiple rings for tighter drug binding. When bound through interactions with the oligopeptide's side chains, the drug may be in a position in which the rings of the drug are either at an angle to or parallel to similar rings in the side chains, so that the aromatic rings on the peptide side chain bind face to face or edge to face or face to edge with the aromatic rings of the drug molecule. Other peptide side chains may be positioned nearby to assist in drug binding through opposite charge interactions. The negatively charged amino acids, glutamic acid or aspartic acid, may be employed to assist in binding the drug doxorubicin (which contains and $NH_3^+$ group), for example.

The oligopeptide may include naturally occurring amino acids that have side chains comprising at least one aromatic ring, e.g., tryptophan, phenylalanine, and tyrosine. Alternatively, an oligopeptide may be synthesized to comprise any other appropriate aromatic ring-containing side chains on the peptide backbone, such as 9-fluorenylmethoxycarbonyl (FMOC), pyrene, rhein, uniblue A, acridine ICR191, histidine-N-dinitrophenyl, or benzyl groups, or even the aromatic portion of the drug of interest. The side chains are chosen for similarity to the structure of the drug to be bound. Aromatic compounds known to precipitate the drug, indicating complex formation, also may be used as side chains (e.g., propranolol for the drug doxorubicin).

As one alternative, the side chains may be attached after synthesis of an oligopeptide sequence. The use of orthogonal protecting groups in synthesis of oligopeptides comprising two or more of the same amino acids will allow synthesis of binding units with different side chains on each of the same amino acid residues, by protecting them with groups which are deblocked under different conditions. Examples of commercially available orthogonal groups include p-methylbenzyl and acetamidomethyl for cysteine, and 2,6-dichlorobenzoxycarbonyl, FMOC, or trifluoroacetyl for lysine.

Conjugatable aromatic groups which can be easily attached to cysteine, lysine, aspartic acid, glutamic acid, serine, threonine, or arginine residues in a peptide chain have been described by Richard Hargland in *Handbook of Fluorescent Probes and Research Chemicals* (1985), available from Molecular Probes, Eugene, Oreg. For example, an aromatic compound comprising an alkyl iodide or maleimide group may be reacted with a cysteine residue in an oligopeptide, thereby attaching the aromatic compound to the peptide backbone as a side chain. Aromatic compounds including but not limited to those comprising aromatic isothiocyanates, sulfonyl chlorides, succinimidyl esters, dichlorotriazinyl groups, or alkyl halide nitrobenzoxadiazole derivatives may be reacted with lysine residues. Aromatic compounds containing amine groups may be attached to aspartic acid or glutamic acid residues using carbodiimide coupling reagents. Aromatic compounds containing glyoxal, phenyl glyoxal, or dicarboxaldehyde groups are reactive with arginine residues.

Examples of some of the many such aromatic compounds which may be attached as side chains to certain amino acid residues are the following:

Thiol Reactive (for Attachment to Cysteine Residues)

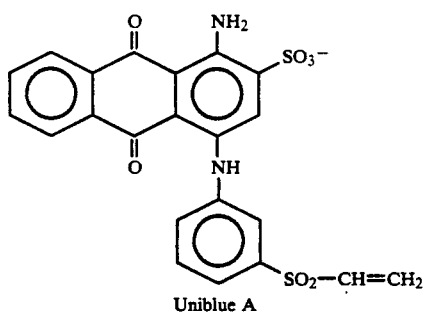
Uniblue A

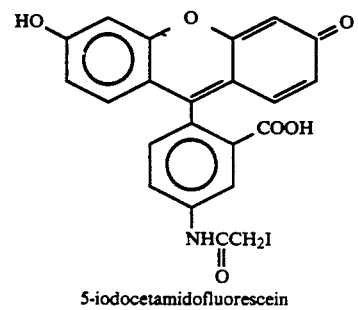
5-iodocetamidofluorescein

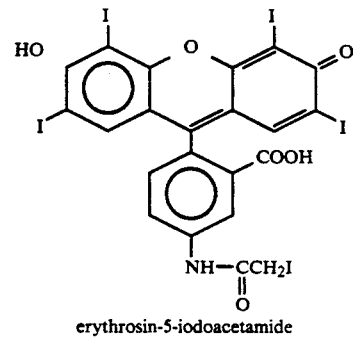
erythrosin-5-iodoacetamide

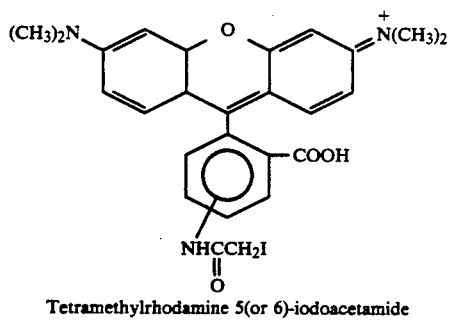
Tetramethylrhodamine 5(or 6)-iodoacetamide

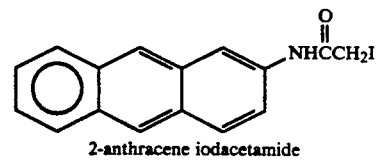
2-anthracene iodacetamide

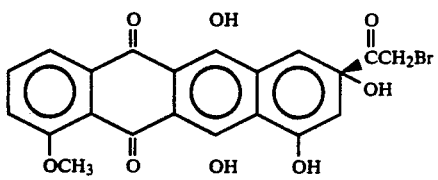

-continued
brominated daunomycin aglycone

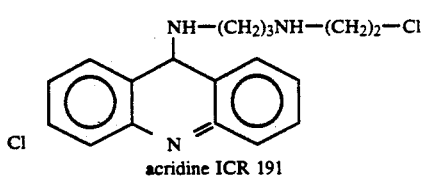
acridine ICR 191

Amine Reactive (Lysine Residues)

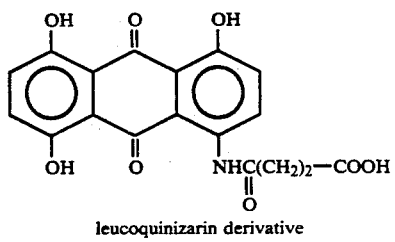
leucoquinizarin derivative

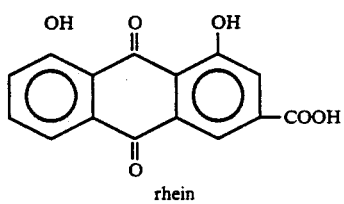
rhein

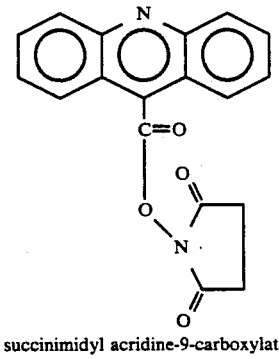
succinimidyl acridine-9-carboxylate

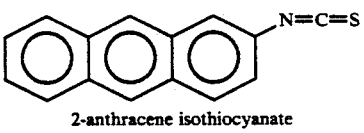
2-anthracene isothiocyanate

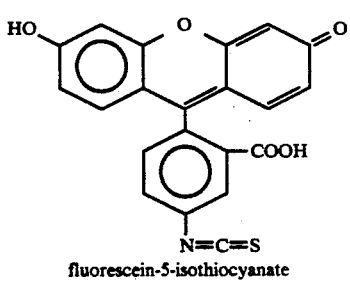
fluorescein-5-isothiocyanate

These aromatic compounds may be suitable for noncovalent binding of the anthracycline antibiotics doxorubicin and daunorubicin, which are widely used in cancer therapy and have the following structure:

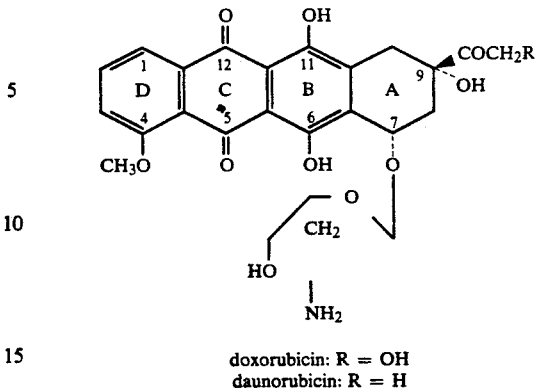

doxorubicin: R = OH
daunorubicin: R = H

Other aromatic compounds which may be attached to a peptide as a side chain are purines, pyrimidines, or analogs thereof. Appropriate longer oligopeptides may incorporate the cognate bases (i.e., guanine, cytosine, thymine, and adenine), which, after refolding and hydrogen bonding, might mimic double-stranded extended DNA for effective intercalation. Doxorubicin is among the drugs known to intercalate within DNA; thus the synthetic peptide would be acting as a DNA analog for purposes of intercalation.

Individual oligopeptide binding units may be combined into longer peptide carriers to increase the stoichiometry of non-covalently bound drug per antibody. If peptide carriers are insoluble when drugs such as doxorubicin are bound, solubility may be increased both by using more soluble aromatic side chains on the peptide or by including more charged amino acid residues per binding unit, such as glutamic acid or aspartic acid.

In one embodiment of this invention, the conformation of the drug-binding oligopeptide is controlled to enhance the intercalation properties of the oligopeptide, and thus to bind the drug more tightly. In an alpha helix, the aromatic drug-intercalating unit is $-X_1-AA_2-AA_3-AA_4-X_5-$ where each AA represents an amino acid and $X_1$ and $X_5$ each represent an amino acid with an aromatic side chain designed to ring-stack or intercalate with the drug to be bound. With the binding unit in this conformation the X groups are on the same side of the helix, nearly on top of each other, about 5.4 angstroms apart. This shorter distance can be adjusted upon drug binding by distortion of the helix to better accommodate bound drug. The $\alpha$ helical conformation is enhanced by inclusion of helix forming residues (and exclusion of helix-breaking residues such as gly or pro) (Chou and Fasman, *Biochemistry* 13:222–245, 1974); the inclusion of glu-lys pairs in i, i+4 positions (i.e., 1,5 positions) of the chain (Marqusee and Baldwin, *Proc. Natl. Acad. Sci.* 84:8898–8902, 1987) and by the elimination of positive charges at the N- and C- termini, respectively (Shoemaker et al., *Proc. Natl. Acad. Sci.* 82:2349–53, 1985), by N-acetylation and conjugation to the carrier protein via the C- terminus (or vice versa).

A drug-binding oligopeptide having a 3–10 helix conformation in which the binding unit is $-X_1-AA_2-AA_3-X_4-$ and the spacing between the X groups is about 6.0 Å, also may be used. In this conformation there are 3.0 residues per helix turn (there are 3.6 residues/turn for the $\alpha$ helix) and thus the intercalating groups will be directly stacked, one turn (6.0 Å) apart. This chain conformation is encouraged by frequent inclusion in the peptide of gamma-aminoisobutyric acid (June, G. et al.

in *Peptides, Chemistry and Biology*, Garland R. Marshall ed. 1988, pp. 37-38), the exclusion of helix-breaking residues such as gly or pro, the inclusion of helix-forming residues, inclusion of glutamates in an i, i+4 spacing to destabilize an α helix at neutral pH (Subbarao, N. K. et al. *Biochemistry* 26:2964-72, 1987), and inclusion of glu-lys pairs in an i,i+3 spacing in the chain.

A beta-sheet conformation is also useful for intercalating aromatic drugs such as doxorubicin or daunorubicin. In this conformation the intercalating unit is $X_1$-$AA_2$-$X_3$- and the approximate distance between X groups is 6.95 Å. In this conformation the X-groups are on the same side of the sheet and thus available for intercalation. This conformation is favored by exclusion of helix-forming residues such as ala, glu, met, lys, and leu; inclusion of beta sheet-forming residues (Chou and Fasman, ibid.); and inclusion of the sheet-forming residues in an alternating sequence of polar and nonpolar residues. Residues with very nonpolar side chains, such as phe, trp or ile, are less frequently included to avoid insolubility of the oligopeptide.

The variable spacing between the X groups can accommodate either face-to-face intercalation (favored by the closer spacing of the α helix or 3-10 helix) or face-to-edge intercalation of the aromatic rings of peptide side chains and drug (favored by the spacing in the 3-10 helix and beta sheet). Thus this system provides binding units for aromatic drugs of differing structures which would favor either mode of intercalation. The conformations will be stabilized by longer oligopeptides for the two helices since helix formation is cooperative. Thus multiple binding units can be included in a single oligopeptide to increase the stoichiometry of drug delivery for each antibody or other targeting protein while increasing the stability of the preferred conformation. For an α-helix which binds drug, for example, if the effect of the X groups (as determined experimentally by circular dichroism, for example) is to destabilize an alpha helix, the ratio of helix-forming residues to binding units can be increased as necessary to stabilize the α-helical chain conformation. Similar examples can be constructed for the other two conformations.

The defined chain conformations suggest appropriate positions for "helper" residues. Doxorubicin binding, for example, appears to be enhanced by inclusion of asp or glu immediately outside the blinding unit for oligopeptides already examined. In an α-helical peptide, for example, the "helper" glu at an appropriate position to ion-pair with the daunosamine positive charge may be that which is closest in space, i.e., in an i,i+4 spacing to the X group. Likewise, the i, i+3 spacing for inclusion of an asp or glu outside the binding unit of a 3-10 helical peptide, and i, i+2 spacing for a beta sheet peptide.

Examples of oligopeptides of defined conformation for intercalation (and thus binding) of an aromatic drug, such as doxorubicin or other anthracyclines, include the α-helix N-acetyl-EAAEXAKAXEAEAAKKAAEA-EXAKAXEAAEK-amide where X, A, E, and K, respectively, are lys-epsilon-FMOC, ala, glu and lys; the 3-10 helix JEXJJXEJEXJJXEJEXJJXEJE where J=α-amino isobutyric acid, and the beta sheet VDVDVNXDXNEDVDVGG where V, D, G and N are val, asp, gly and asn.

Peptides with consecutive glutamates may be hydrolyzed in lysosomes by glutamate hydrolase after entry of the antibody conjugate into cells, resulting in release of the drug if these residues are important for ion pair formation. Likewise, exposure to lysosomal carboxypeptidases may also enhance drug release after internalization. Another possibility involves insertion of consecutive alanines which may be susceptible to lysosomal elastase hydrolysis.

The oligopeptides may be synthesized using any of a number of known procedures. When desired, additional side chains may be attached to certain amino acid residues after synthesis of the oligopeptide, as described above. Peptide amides can be made using 4-methylbenzhydrylamine-derivatized, cross-linked polystyrene-1% divinylbenzene resin and peptide acids made using PAM (phenylacetamidomethyl) resin (Stewart et al., "Solid Phase Peptide Synthesis," Pierce Chemical Company, Rockford, Ill., 1984). The synthesis can be accomplished either using a commercially available synthesizer, such as the Applied Biosystems 430A, or manually using the procedure of Merrifield et al. (*Biochemistry* 21:5020-31) 1982, or Houghten (*PNAS* 82:5131-35, 1985). The side chain protecting groups are removed using the Tam-Merrifield low-high HF procedure (Tam et al., *J. Am. Chem. Soc.* 105:6442-55, 1983).

The peptide can be extracted with 20% acetic acid, lyophilized, and purified by reversed phase HPLC on a Vydac C-4 Analytical Column using a linear gradient of 100% water to 100% acetonitrile-0.1% trifluoroacetic acid in 50 minutes. The peptide is analyzed using PTC-amino acid analysis (Heinrikson et al., *Anal. Biochem.* 136:65-74, 1984). After gas-phase hydrolysis (Meltzer et al., *Anal. Biochem.* 160:356-61, 1987), sequences are confirmed using the Edman degradation or fast atom bombardment mass spectroscopy.

The oligopeptide may be designed to comprise an amino acid residue (generally at the N- or C-terminus of the peptide) through which the oligopeptide can be joined to a targeting protein, such as cysteine or lysine. When necessary, this residue may be orthogonally protected, and deprotected just before or during reaction with the protein. An example would be (nitropyridenesulfenyl) cysteine. The oligopeptide may be attached to a targeting protein (preferably after drug binding) using any of a number of known bifunctional cross-linking reagents. The choice of cross-linking reagent depends on the amino acid sequence of the oligopeptide. If the oligopeptide contains a lysine residue, amine-reactive, bifunctional cross-linking reagents such as bis(sulfosuccimidyl) suberate may be used. Alternatively, a water-soluble carbodiimide coupling reagent may be used to form bonds between a free amino group on one reactant (i.e., the oligopeptide or the targeting protein) and a COOH group on the other reactant.

The following examples are designed to illustrate the concept of drug-binding molecules of complementary structure. The examples use the drug doxorubicin, whose structure is illustrated in FIG. 1 as the model neoplastic drug. Doxorubicin is chosen for these illustrative purposes because it is an approved drug that is effective against a number of tumors; it is widely available; and its chemotherapeutic mode of action, its pharmacology and its pharmacokinetics have been studied. Additionally, doxorubicin is also often used as a model chemotherapeutic drug in studies of drug interactions with biological compounds.

The following examples are offered by way of illustration and not limitation.

EXAMPLE 1

A csDBM for Doxorubicin

In many of the examples, a naturally occurring csDBM structure is used. This structure binds to the drug doxorubicin. Flavin mononucleotide (see FIG. 1) in its reduced state has functionalities which hydrogen bond to the carbonyl and hydroxyl groups of doxorubicin and undergo ionic interactions between the negative phosphate groups on the FAD and the amino group on the daunosamine sugar, and pi bonding between the planar rings. Accordingly, FAD is a csDBM to doxorubicin.

EXAMPLE 2

Preformed Method of csDBM-Drug Conjugation

In this approach, drug is first complexed with an "activated" csDBM and then conjugated to antibody. The csDBM is first derivatized with a nucleophilic group such as a maleimide, which can bind to reduced sulfhydryl groups on the antibody molecule. This conjugation is initiated by the step of mixing doxorubicin with FAD in an aqueous, neutral pH buffer (which is slightly hypotonic). The csDBM is used at a concentration to initially promote 1:1 complexes between drug and csDBM (equimolar offering). Initial binding of the drug and csDBM may be promoted by the addition of a dehydrating agent, such as ten percent ammonium sulfate. The drug is added at relatively high concentrations, such as 2 to 4 mg/ml. This results in a larger proportion of the csDBM being complexed by multiple non-covalent interactions with the drug, with a small proportion of precipitated drug.

Upon complexation, the hydrogen bonding, ionic bonding, and pi-pi interactions stabilize the complex. Following complexation, the complex is offered to antibody at 10- to 100-fold molar excess of drug csDBM to antibody at room temperature for 1 hour. Antibody, such as a monoclonal antibody, is prepared for conjugation by reduction with dithiothrietal (DTT) (See Example 4).

Unbound drug/csDBM is then removed by dialysis or gel filtration. Six to ten drug/csDBM complexes per antibody will be bound with direct conjugation or 15–40 complexes via a carrier such as albumin.

EXAMPLE 3

Post-Formed Method of csDMB/Drug Conjugation

In one example, FAD is coupled directly to antibody. Thus, 1 mg of antibody is mixed with 2 mg FAD (5 mg/ml). The solution is warmed to 37° C. in a water bath, and 2 mg of EDCI (1-ethyl-3-(3-dimethyaminopropyl)-carbodimide) at 10 mg/ml is added. The pH is adjusted to approximately 6.0 with 1N HCl and the reaction stirred for approximately 20 minutes at 37° C. 0.7 ml of 0.05M PBS (pH 9.0) is added to the reaction until the pH is 8.0–8.5 and mixed. Then 100 μl of 0.25% glutaraldehyde (Type I—Sigma Chemical Co., St. Louis, Mo.) is added slowly with stirring for 10 minutes. The conjugate is then purified from reactants by gel filtration in phosphate buffered saline (PBS) and concentrated by ultrafiltration and washed at least twice in 2 volumes of PBS. Typically, 10 FAD/antibody are conjugated via this approach. Doxorubicin is reacted at 100 molar excess at 37° C. for 60 minutes and continued at 4° C. overnight. Free drug is removed from antibody-csDBM-drug conjugate by a combination of gel filtration and ultrafiltration. Typically, one mole of drug is incorporated per FAD molecule conjugated to antibody.

A second example of using a csDBM conjugation uses a dye, such as Reactive Blue 4 (RB4) (Aldrich Chemical Co.) coupled first to human serum albumin (HSA) and then conjugated to antibody. 2.6 mg of human serum albumin (at 10 mg/ml) at pH 8.5 in 0.2M bicarbonate buffer is reacted with 7.5 mg of activated RB4 (which reacts by alkylation of amino groups on protein by the chloro group on RB4. The RB4 at 20 mg/ml in $H_2O$ is reacted for 1 hour at room temperature. 1.0M lysine at approximately pH 10 is used to quench the reaction. The conjugate is "cleaned up" by gel filtration, resulting in approximately 7 RB4 molecules/human serum albumin (HSA). The derivatized albumin is then reacted with 1 mg of SMCC in 10% DMSO/ethanol at pH 9.8 for 1 hour at room temperature. Excess reactants are removed by gel filtration. Antibody (10 mg) is reacted with 8 mg DTT at room temperature for 30 minutes. Excess reactants are removed by gel filtration in degassed PBS and antibody (now bearing free SH groups) reacted with the SMCC derivatized albumin. The conjugate is then reacted with a 100 molar excess of doxorubicin overnight at 4° C., followed by the removal of the unbound drug.

EXAMPLE 4

Assessment of csDBM/Drug Affinity

Affinity of binding of drug bound to soluble csDBM or to csDBM conjugated to antibody or carrier can be assessed, for example, by competition with albumin or cardiolipin-containing liposomes. Cardiolipin is a strong acceptor of doxorubicin. Doxorubicin associated with liposomes is measured spectrophotometrically. Doxorubicin associated with albumin is also measured spectrophotometrically. Once albumin is separated from antibody by differential $(NH_4)_2SO_4$ precipitation or binding to Cibracron Blue Sepharose, the two drug acceptors are used to challenge the drug bound to antibody or carrier and represent the dissociation rate in serum or at target cell membranes. As an example, doxorubicin bound to the reduced form of flavin adenine dinucleotide on antibody or carrier shows no reduction in bound doxorubicin when challenged with albumin, but shows transfer of doxorubicin to cardiolipin liposomes. Reducing the number of bonds by using oxidized flavin adenine dinucleotide allows for more rapid transfer to cardiolipin-containing liposomes but still only a low level transfer to albumin. This system is used to test for the appropriate affinity of csDBM-drug interaction and allows one to know, in advance, whether or not the number of non-covalent bonds in a drug/csDBM complex results in an appropriate affinity for delivery and release of drug at tumor sites. In some cases where the acceptor is unknown, membranes prepared from appropriate target cells could be used as the competitor.

A second methodology allows one to approximate the cumulative non-covalent bond energy between csDBM and drug. A number of current chemotherapeutic drugs are charged at physiologic pH. Doxorubicin is positively charged due to the amino group of the daunosamine sugar. When analyzed on an isoelectric focusing agarose gel, doxorubicin migrates to the cathode and can be readily visualized. When complexed with a csDBM that stably and non-covalently binds doxorubicin and satisfies ionic interaction, the drug/csDBM complex remains at the origin in an isolectric-focusing agarose gel. By adjusting the electrical field strength until dissociation of drug and csDBM occurs, one indirectly tests the affinity of binding between csDBM and drug.

EXAMPLE 5

Potency and Selectivity Immunoconjugates of Drug/csDBM

Potency and selectivity of drug conjugates can be measured by in vitro cytotoxicity assays versus antigen-positive and antigen-negative cells. One such assay utilizes MTT dye uptake and metabolism to determine residual surviving cells.

Figure 2:
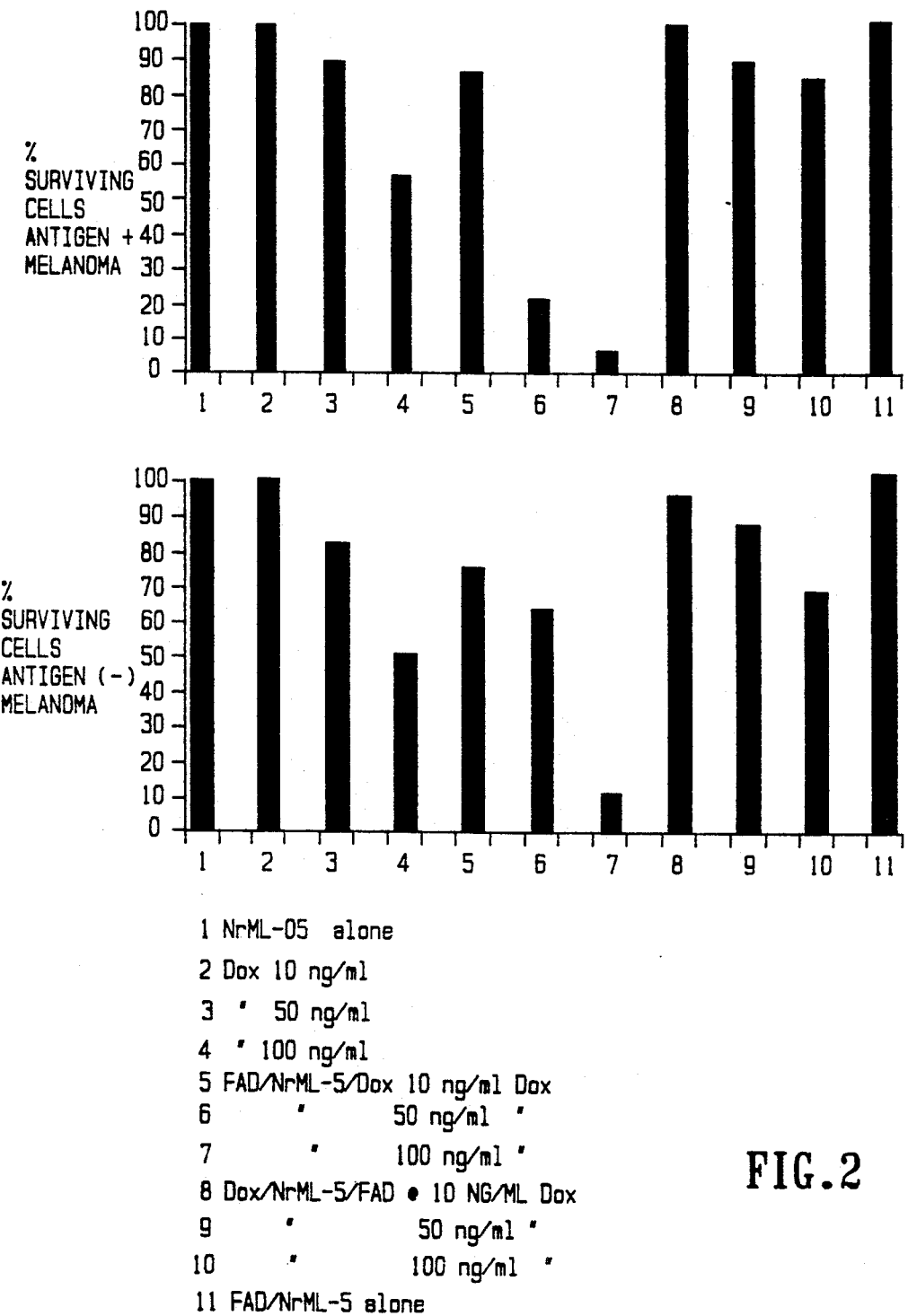

Potency and selectivity of covalent and non-covalent antibody-csDBM-drug conjugates of doxorubicin are illustrated in FIG. 2. Two types of covalent conjugates are used as benchmarks. The first is a conjugate of doxorubicin that uses ECDI as the cross-linking agent. In the second case, doxorubicin is bound through the amino group of the daunosamine sugar to antibody via a cross-linking reaction with glutaraldehyde. The ECDI-bonded, non-metabolizable conjugate is the least potent of the three types of antibody conjugates on a mole/mole basis when compared to free drug on the same cell line. The amino-bonded conjugate gives higher potency values but shows no selectivity on an antigen-negative cell line. The csDBM-drug immunoconjugate has higher potency that the free drug, and has better selectivity than the covalent conjugates. These results indicate that conjugation utilizing non-covalent interactions such as pi-pi ionic and hydrogen bonding of the drug to the csDBM creates both a potent as well as a more selective conjugate.

Selectivity is improved, because the csDBM occupies the functional groups of the drug and interacts with cell membranes in a non-antigen-specific manner. Upon binding of the antibody to cell surface antigens, the juxtaposition of the non-covalently bound drug with the lipid membrane of the cell is sufficient to cause the detachment of the doxorubicin and the transfer of the drug to acceptor sites within or upon the plasma membrane.

EXAMPLE 6

Drug Conjugation to Partial or Pre-existing csDBMs on a Carrier

In this example, albumin which has both low affinity as well as fewer high affinity sites for doxorubicin is exposed to 100 moles of drug per mole of protein in the presence of a dehydrating agent as indicated in Table 1. Without the dehydrating agent <2 moles of drug is bound/albumin and drug leaches rapidly. With the use of dehydrating agent 6–15 moles of drug are bound per mole of protein with both low and high affinity (e.g., rapid or slow leaching). The conjugate, after removal of excess free drug, is lyophilized and reconstituted as a typical pharmaceutical and administered as a slow release form of doxorubicin.

The number of high affinity sites on albumin is increased by conjugation of an activated form of cardiolipin on AZP to albumin. Some of these "partial" csDBMs will be in juxtaposition to other functional groups of endogenous amino acids which will complete the drug-binding structure. Conjugation of drug is carried out as above and results in drug/carrier conjugate with slower release properties.

EXAMPLE 7

Pharmaceutical Preparations of Soluble Drug/csDBMs

In most cases, drugs such as doxorubicin are complexed with csDBM either in the presence or absence of a dehydrating agent such as in Example 2. If a dehydrating agent is used, one compatible with intravenous administration like ethylene glycol is preferable. As with the csDBM, FAD, if conjugation to protein is not intended, additional functional group(s) are available to undergo further interaction with the drug producing higher affinity binding. Upon challenge with cardiolipin-liposomes only slow transfer kinetics are seen. These results correlate with reduced cardiac toxicity, in vivo, of the doxorubicin/csDBM complex.

EXAMPLE 8

Doxorubicin is covalently conjugated to NR-ML-05, a monoclonal antibody specific for the 250 kilodalton melanoma-associated antigen. The mechanism of covalent conjugation is well established in the field. Oxidized FAD, non-oxidized FAD, propranalol or other csDBMs for doxorubicin are added, and then dialyzed. The drug conjugate with non-covalently bound csDBM is evaluated against antigen positive (M14+) and antigen negative (M14−) cell lines and is compared for selectivity in vitro by comparing IDSO values for the M14+ and M14− cells to free doxorubicin and to the doxorubicin-NR-ML-05 conjugate without csDBM. The csDBM is chosen that provides potency as close as possible to the conjugate not complexed with csDBM, but also provides the most selectivity as defined by the in vitro assay. The csDBM must bind to the drug or the antibody with sufficient stability, however, to remain complexed in human serum.

In another embodiment mitomycin-C is bound covalently to an antibody. FAD, oxidized FAD, propranalol or other csDBMs are added, and then the unbound csDBM is dialyzed out. The conjugate of mitomycin-C is tested against antigen positive and antigen negative cells and compared to those conjugates that have been exposed to the different csDBMs. The procedure permits the selection of the most cytotoxic conjugate.

EXAMPLE 9 csDBMs to 5-Fluorouracil (5-FU)

A csDBM to 5-FU is made by modifying the side chain of Thiamin (vitamin $B_1$) to make it susceptible to covalent binding to a targeting protein while retaining the intact functional groups on the pyrimidine ring so as to non-covalently bind 5-FU through multiple interactions. The synthetic scheme to make compound 7, the 2,3,5,6-tetrafluorophenyl ester of 4-β-(N-γ-carboxy propionyl) aminomethyl-5-methyl-1-N-(R-methyl-4-aminopyrimidine-5-yl) methyl thiazole, is depicted in scheme 1 below.

Scheme 1

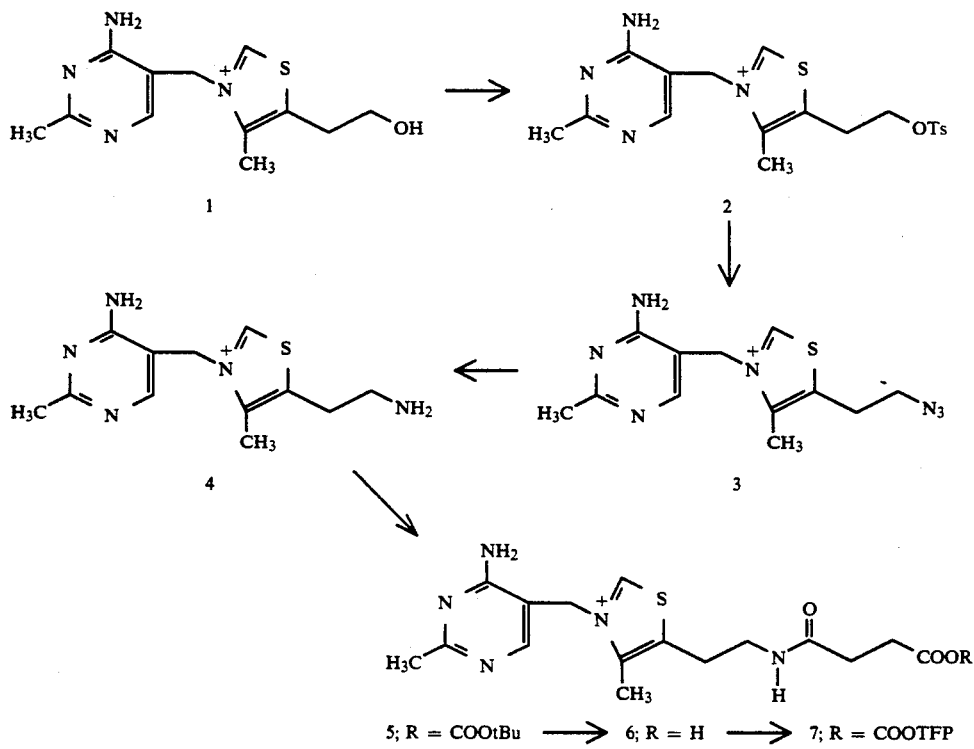

5; R = COOtBu ⟶ 6; R = H ⟶ 7; R = COOTFP

A solution of thiamin (compound 1 in Scheme 1) is dissolved in 5 mL of anhydrous pyridine and cooled to 0° C.–5° C. p-Toluenesulfonyl chloride (1.1 mmole) is added in portions over a period of 5–10 minutes. The solution is stirred while refrigerated for 2–3 hours and can be stored overnight if kept refrigerated. Approximately 5–10 mL of water is added and the solution may be filtered, if necessary. If no precipitate forms, the solution is evaporated to dryness in vacuo. The dried residue is dissolved in ethyl acetate. The dissolved residue is washed with water and then dried over anhydrous sodium sulfate and evaporated to dryness to yield the product, O-p-toluenesulfonyl thiamin, depicted as compound 2 in Scheme 1.

Compound 2 is made into a 1 mmolar solution in 10 mL of anhydrous tetrahydrofuran. Trimethylsilyl azide (1.2 mmoles) is added to the solution and then the solution is refluxed for 6–8 hours. The solution is evaporated to dryness and then the remaining residue is dissolved in ethyl acetate. The new solution is washed with water and then dried over anhydrous sodium sulfate followed by evaporation to yield 4-β-Azidoethyl-1-N-(2-methyl-4-amino pyrimidin-5-yl)methyl thiazole shown as compound 3 in Scheme 1. Compound 3 is purified by preparative liquid chromatography.

Compound 3 (1.0 mmole) in 10–15 mL of absolute ethanol, is hydrogenated at atmospheric pressure over sulfided Pd-C catalyst in a Paar apparatus. After hydrogenation, the catalyst is removed by filtration over celite and the solvent is removed in vacuo, leaving 4-β-Aminomethyl-1-N-(2-methyl-4-aminopyrimidinyl)-methyl-5-methyl thiazole or Compound 4 in Scheme 1.

Compound 4 (1.0 mmole) is dissolved into 10 mL of anhydrous tetrahydrofuran and succinic acid mono-t-butyl ester mono succinimidate ester is added. The solution is mixed and then stirred for 2 hours at room temperature. The solvent is next evaporated. The residue is dissolved in methylene chloride and then washed with water. The organic layer is dried with anhydrous MgSO4 and then evaporated to yield the derivative of compound 4 which is compound 5 in Scheme 1.

Compound 5 is converted to the free acid form by adding the t-butyl ester (1 mmole) to 10 mL of methylene chloride and 2 mL of anhydrous trifluoroacetic acid and the solution is stirred for 30 minutes under refrigeration conditions. The solution is allowed to warm to room temperature while the stirring is continued for another 3 hours. The solvents are removed in vacuo and the residue is coevaporated several times with methylene chloride to ensure the complete removal of trifluoroacetic acid. Trituration with ether precipitates the free acid, which is compound 6 in Scheme 1. Compound 6 is purified by liquid chromatography.

The 2,3,5,6-tetrafluorophenyl ester of the free acid is formed from a solution of 1 mmole of free acid (compound 6) dissolved in 10 mL of acetronitrile:water (4:1), 3 mL of tetrafluorophenol and 5 mmole of 1-(3-dimethylaminopropyl)-3-ethylcarbodimide hydrochloride and the resulting solution is stirred overnight at room temperature. The precipitated solid is filtered and then washed with ether to remove the free tetrafluorophenyl. The active ester is purified by high pressure liquid chromatography and is compound 7 in Scheme 1.

EXAMPLE 10

A Modified FAD AS A Doxorubicin Antimer

In this example, a modified FAD is made to become a csDBM to doxorubicin. The resulting csDBM, a riboflavin derivative, contains binding sites for non-covalent interactions with doxorubicin and an active ester leaving group for covalent attachment to the targeting protein. The synthetic scheme for making the modified FAD csDBM is illustrated in Scheme 2 below.

Scheme 2

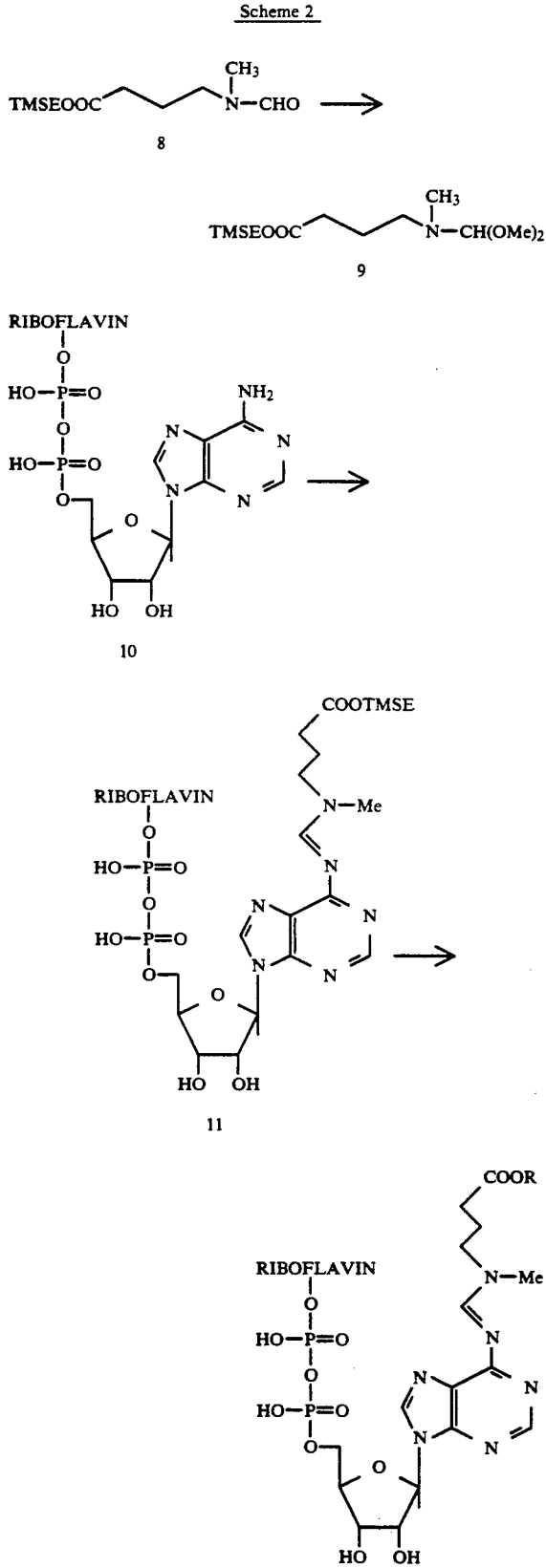

-continued
Scheme 2

12; R = COOH
13; = COO-Active Ester

Compound 8 in Scheme 2 is formed by mixing a solution of 2 mmole of 4-(methylamino)butyric acid in 10–15 mL of formic acid and 2–3 drops of acetic anhydride. The mixture is stirred for 30 minutes. The solvent is evaporated and titrated with ether to yield the product of the reaction, N-formyl-4-(methylamino)butyric acid, which in the quantity of 1 mmole is added to anhydrous tetrahydrofuran and stirred with 1.1 mmole of trimethylsilyethanol (TMSE) from Aldrich Chemical, and 1.1 mmole of N,N'-dicyclohexylcarbodiimide for an overnight time period. A precipitated solid will be formed. The solid is filtered and the filtrate is evaporated to dryness. The residue is dissolved in ethyl acetate and washed with water. The organic layer is dried and evaporated to give N-formyl-4-(methylamino)-butyric acid trimethylsilylethyl ester, and the ester (compound 8) is refluxed with methanol (20 mL/mmole of the compound) containing a catalytic amount of p-toluenesulfonic acid for 5–6 hours. The methanol is completely removed in vacuo and compound 9 in Scheme 2 is purified by column chromatography.

FAD (flavine adenine dinucleotide, Pierce Chemical; compound 10) 1 mmole is dissolved in 20 mL of acetonitrile:water (1:1) and compound 9 of Scheme 2, N-dimethoxymethyl-N-methyl-4-(methylamino)butyric acid trimethylsilyl ethyl ester (2–3 mmole) is added and the mixture is stirred for 6–10 hours at room temperature. The solvents are removed in vacuo and the residue is suspended in water and extracted with ethyl acetate to remove the excess of compound 9. The product, flavin $N^6$-(methyl,$\gamma$-carboxy-propyl) aminomethylene adenosyl dinucleotide, compound 11 in Scheme 2 is isolated from the aqueous solution by freeze-drying followed by liquid chromatography purification.

A 1 mmole concentration of compound 11 is dissolved in 2 mL of triethylammonium bicarbonate and then evaporated to dryness. Approximately 5 mL of water is added to the residue and 2 mmole of potassium fluoride or tetraethyl ammonium fluoride is also added and the mixture is stirred for approximately 30 minutes. The mixture is evaporated to dryness. Acetone is added and then the solution is coevaporated. The residue is dissolved in 1:1 ethanol-acetone mixture to which a saturated solution of $NaClO_4$ is added and the mixture is stirred for approximately 30 minutes. A solid is precipitated and isolated by centrifugation and then dried in a vacuum desiccator and purified by liquid chromatography by using isopropanol-acetic acid-water as mobile phase.

One mmole of the free acid compound 12 is added to 5 mL of acetonitrile:water (1:1) and 3 mmole of 2,3,5,6-tetrafluorophenol and 3 mmole of 1-(3-dimethyl-aminopropyl)-3-ethylcarbodiimide hydrochloride is added to the solution and the solution is stirred for 10–12 hours at room temperature. The solution is diluted and extracted with ether to remove excess tetrafluorophenol and the product, flavin $N^6$-(methyl1-2,3,4,5,6-tetrafluorophenoxycarbonylpropyl) aminomethylene-adenosyl dinucleotide, compound 13 in scheme 2, is isolated by high pressure liquid chromatography.

EXAMPLE 11 csDBM for Methotrexate

A csDBM to methotrexate (MTX) can be formed that utilizes both ionic interactions and hydrogen bonding interactions to non-covalently bind MTX to the csDBM. Methotrexate will non-covalently bind to the csDBM via its pteridine ring to the pyridophyrimidine ring of the csDBM and with the pyrolidine ring of MTX to the α carboxylic acid of the glutamic acid portion of the csDBM. Scheme 3 below illustrates the synthetic procedure necessary to form the csDBM α-1-piperdinyl-α-N-p-(2,4,8 trioxopyrido [3,2-d] pyrimidin-6-yl) acetylphenyl amido glutaric acid-γ-succinimidate ester.

Scheme 3

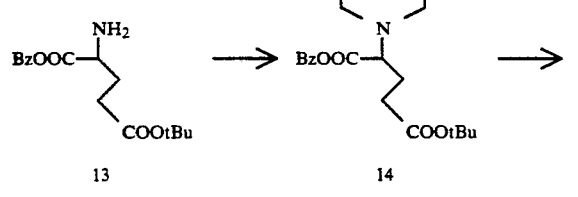

Bz = C₆H₅—CH₂—

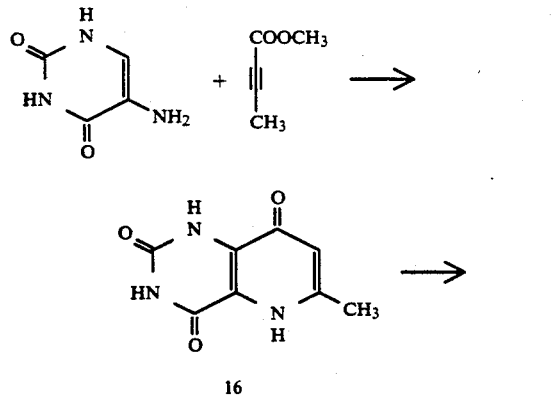

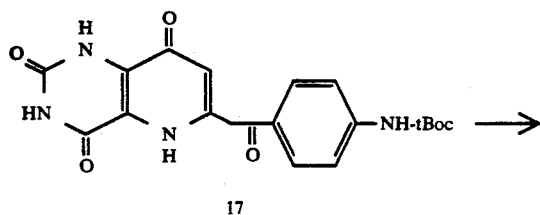

Scheme 3 -continued

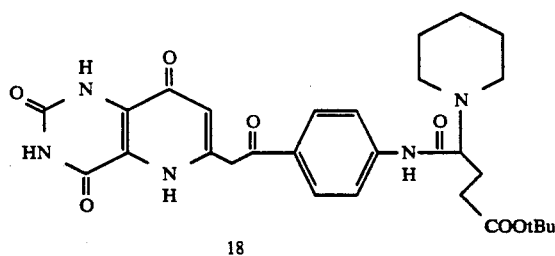

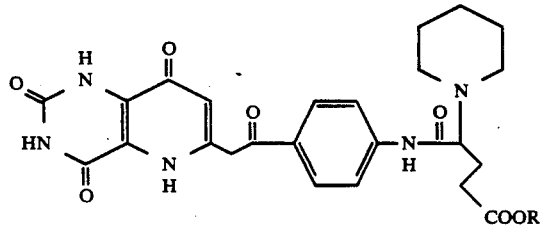

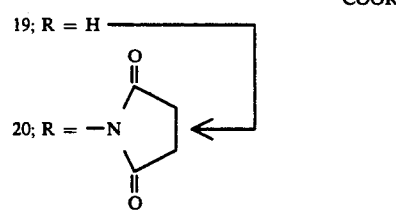

A 5 mmole concentration of compound 13, glutamic acid-α-benzyl ester-γ-t-butyl ester is added to 5 mL of a 25% solution of glutaraldehyde and the solution is stirred for 2–3 hours at room temperature. To this solution is added 10 mmoles of sodium cyanoborohydride and the stirring is continued for another 2 hours. The aqueous phase of the solution is evaporated and the residue is suspended in water and extracted with ethyl acetate. The organic layer is washed with water, dried over anhydrous sodium sulfate and then evaporated to give compound 14. Compound 14, 2-(pyrrolidin-1-yl)-glutaric acid-1-benzyl ester-5-t-butyl ester is purified by preparative liquid chromatography.

A solution of 2 mmole of compound 14 is prepared in 20 mL of methanol containing two equivalents of hydrogen chloride and hydrogenated in a Paar apparatus over Pd-C (10%) for 3 hours. The catalyst is filtered through celite and the filtrate is evaporated to give the product, compound 15, as a hydrochloride salt.

To a suspension of 10 mmole of 5-aminouracil in 100 mL of methanol is added 12.5 mmole of methyl-2-butynoate and the suspension is stirred at room temperature for 8 hours. The precipitated solid is filtered and dried in vacuo to give 4-(2',4'-dioxopyrimidin-5-yl) amino crotonate. A suspension of the crotonate is refluxed for 3 hours. The mixture is cooled to room temperature and petroleum ether is added. The precipitated solid is filtered and air dried to give compound 16, 2,4,8-trioxo-6-methylpyrido[3,2-d] pyrimidine, which is purified by crystallization.

To a 2 mmole solution of p-aminobenzonitrile in 10 mL of dry dimethylformamide, 3 mmole of di-t-butyl dicarbonate is added and the solution is stirred for 3–5 hours at room temperature. The solvent is removed in vacuo and the residue is suspended in water and extracted with methylene chloride. The organic layer is washed with water, dried with anhydrous MgSO₄ and evaporated to give p-N-t-butoxycarbonylaminobenzonitrile, which is purified by crystallization. A 5 mmole suspension of compound 16 is refluxed with 5 mL of hexamethyldisilazane and 1 mL of chlorotrimethylsilane and 50 mL toluene. After a clear solution is obtained, the solvent is removed with the exclusion of moisture to obtain the trimethylsilyl derivative of compound 16. This derivative is dissolved in 10 mL of anhydrous tetrahydrofuran (THF). The trimethylsilyl derivative of compound 16 in solution is added to a cooled solution of 6 mL of 1 molar n-butyl-lithium in anhydrous THF. A red solution is obtained indicating the formation of α-methyllithium derivative of compound 16. After approximately 30 minutes of stirring, 5 mmole of p-N-t-butoxycarbonylaminobenzonitrile in 5 ml of anhydrous THF is added in drops over a period of 5 minutes. After another 10–15 minutes of stirring, 10 mL of 1N hydrochloric acid is added to hydrolyze the amine formed in the reaction. The solvents are removed in vacuo and the residue is crystallized to give the product, 2,4,8-trioxopyride [3,2-d] pyrimidin-6-yl) methyl-(p-t-butoxycarbonyl)-amino phenyl ketone, compound 17.

Two mmole of compound 17 is dissolved in approximately 10 mL of methylene chloride and 2 mL of trifluoroacetic acid and stirred for 3 hours. The solvents are removed and the residue is titrated with ether to yield an aniline intermediate. A 2 mmole solution of the aniline intermediate is stirred with 2 mmole of compound 15 above in 20 mL of acetonitrile:water (1:1) and 5 mmole of 1-(dimethylaminopropyl)-3-ethyl-carbodiimide. After the reaction is completed the solvents are removed and the product, compound 18, α-1-piperdinyl-α-N-p-(2,4,8- trioxopyrido [3,2-d] pyrimidin-6-yl) acetylphenyl amido glutaric acid-γ-t-butyl ester is isolated by silica gel chromatography. Two mmole of compound 18 is stirred with 10 mL of methylene chloride and 2 mL of trifluoroacetic acid for 3 hours. The solvents are removed and the residue is triturated with ether to give the acid intermediate to prepare the active ester. The acid intermediate is compound 19 in Scheme 3. A solution of compound 19 (1 mmole) in anhydrous acetonitrile is stirred with 1.1 mmole of N-hydroxisuccinimide and 1.1 mmole of N,N'-dicyloatxylcarbodiimide for 10–12 hours at room temperature. The precipitated dicyclohexylurea is filtered and the filtrate is evaporated to dryness. The residue is dissolved in ethylacetate and then washed with water. The organic layer is dried with anhydrous sodium sulfate and evaporated in vacuo to give the product, a csDBM depicted in Scheme 3 as compound 20, which is α-1-piperdinyl-α-N-p-(2,4,8-trioxopyrido [3,2-d] pyridimidin-6-yl)-acetylphenyl amido glutaric acid-γ-succinimidate ester. The final purification is carried out by high pressure liquid chromatography.

EXAMPLE 12 a csDBM for Cytosine Arabinoside (ARA-C)

A csDBM for ARA-C is prepared by designing a molecule which reacts with the nitroisocytidine groups of the ARA-C molecule by ionic interactions and hydrogen bonding. The rest of the csDBM molecule is designed to confer aqueous solubility on the csDBM. The preparation of the csDBM to ARA-C is described in Scheme 4.

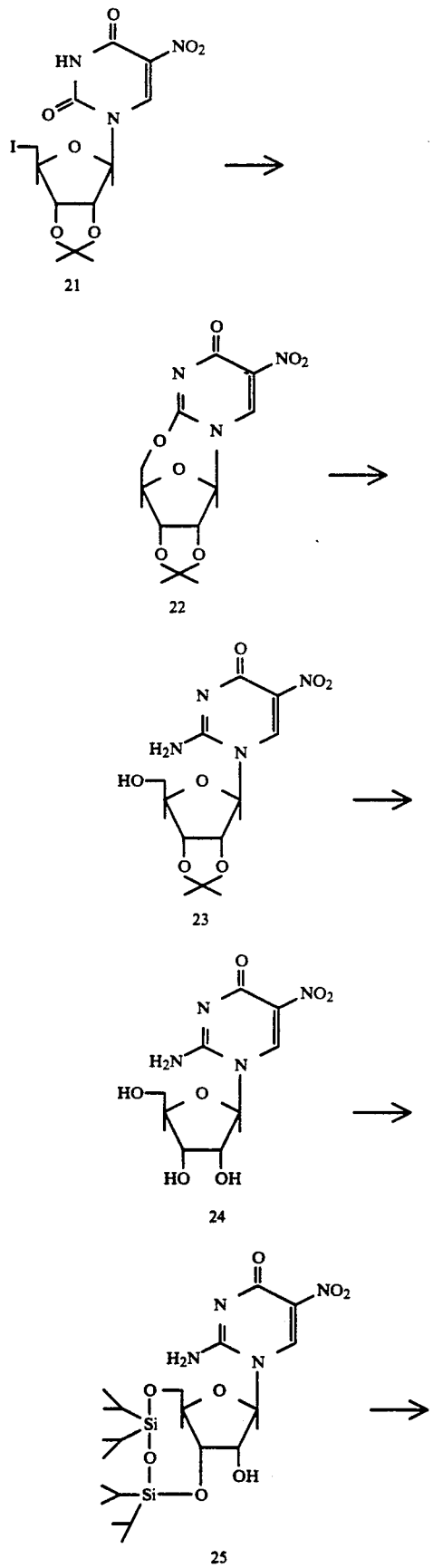

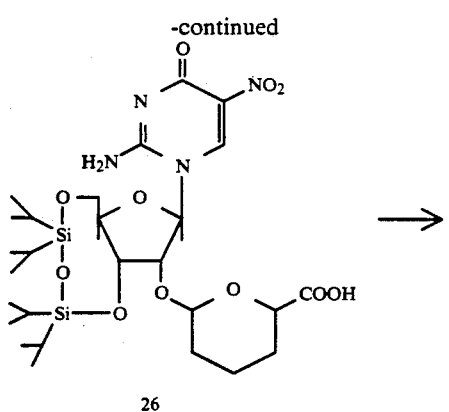

26

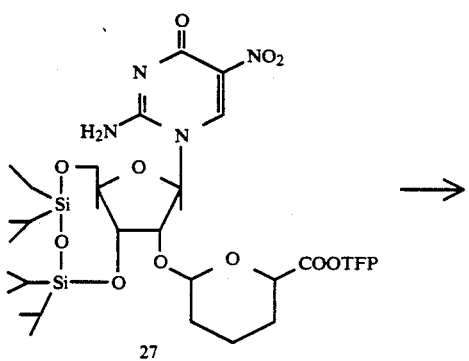

27

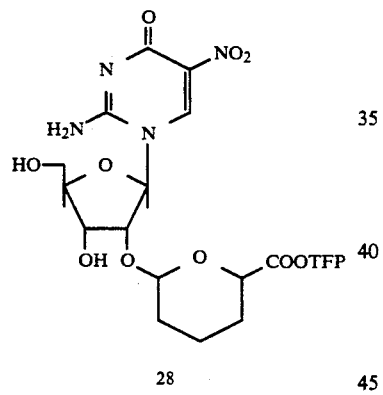

28

Compound 21 of Scheme 4,5'-deoxy-5-iodo-2',3'-0-isopropylidene-5-nitrouridine is prepared by the procedure similar to the one used by Brown et al., *J. Chem Soc.*, 868 (1957), except the starting material is 5-nitrouridine instead of uridine. Compound 21 is converted to 2,5'-anhydro-2',3'-0-isopropylidene-5-nitrouridine which is compound 22 in Scheme 4. Compound 22 is reacted with saturated methanolic ammonia to give 2',3'-0-isopropylidene-nitroisocytidine, which is compound 23. Compound 23 is deprotected using 98% formic acid to give 5-nitroisocytidine, which is compound 24.

A solution of 2 mmole of compound 24 is prepared with 20 mL of anhydrous tetrahydrofuran and containing 2.5 mmole of triethylamine and 1.1 mmole of 1,3-dichloro-1,1,3,3-tetraisopropyldisiloxane in 2 mL of tetrahydrofuran. The solution is stirred for 8 hours and evaporated to dryness. The residue is dissolved in methylene chloride and purified by flash chromatography over silica gel. The residue is compound 25, which is 3',5'-tetraisopropyl-disiloxy-5-nitroisocytidine.

A solution of 1 mmole of compound 25 is prepared in 10 mL of anhydrous THF containing a catalytic amount of p-tolunesulfonic acid, and 1.1 mmole of 3,4-dihydro-2H-pyran-2-carboxylic acid. The solution is stirred for 3–4 hours and then evaporated in vacuo to yield compound 26 which is 6''-carboxy-2'-tetrahydropyran-2''-yl-3',5'-tetra-isopropyl-disiloxy-5-nitroisocytidine.

Compound 26 is purified by column chromatography. The tetrafluorophenyl ester of compound 26 is prepared by the same procedure as described in Example 10. The tetra-fluorophenyl ester of compound 26 is shown in Scheme 4 as compound 27.

One mmole of compound 27 is mixed with 1.1 mL tetra-n-butyl-n-ammonium fluoride in THF with 10% water for 30 minutes. The solvent is removed in vacuo and the residue containing the product, compound 28, 6''-(2,3,5,6-tetrafluorophenoxycarbonyl)-2'-tetrahydropyran-2''-yl-5-nitroisocytidine, compound 28, is purified by silica gel flash chromatography and a final purification by high pressure liquid chromatography.

EXAMPLE 13

A csDBM for Mitomycin-C

Scheme 5 depicts the synthetic procedure to form the active ester csDBM for mitomycin-C.

Scheme 5

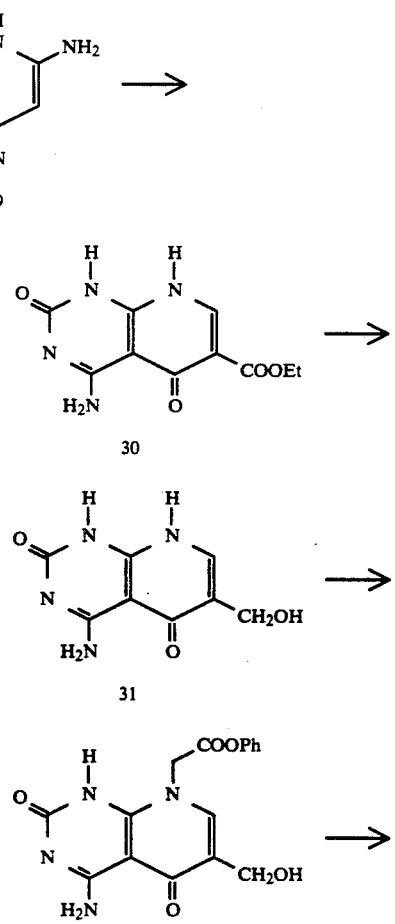

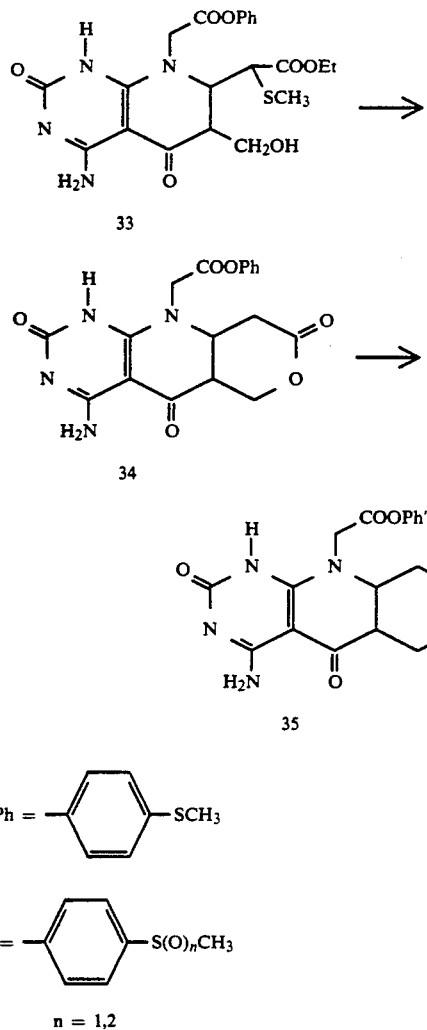

A mixture of 5 mmole of 4,6-diamino-2-oxopyrimidine and 10-15 mmole of diethylethoxymethylene malonate is mixed and heated at 120° C. to 150° C. for 6-8 hours. A clear melt is obtained. The temperature is maintained to facilitate the removal of ethanol. After the ethanol is removed, the mixture is allowed to cool to room temperature and the solid mass is broken up with ethanol and filtered to give the intermediate product, 2-(4-amino-2-oxopyrimidin-6-yl) aminomethylene malonate. The above malonate derivative is stirred and heated in Dowtherm A for 3-5 hours to complete the cyclization yielding product 30 in Scheme 5, 4-amino-6-carbethoxy-2,5-dioxopyrido [2,3-d] pyrimidine. The precipitated solid is filtered, washed with petroleum ether and recrystallized prior to the reduction step.

A suspension of compound 30 in 20 mL of anhydrous THF is made in 2 mmole of LiAlH$_4$ is added in small portions. The progress of the reduction is monitored by TLC (thin layer chromatography). If the reduction is incomplete, portions of the LiAlH$_4$ is added to complete the reaction. A small quantity of ice-cold water is added in drops to destroy the excess reagent and then is filtered out. The filtrate is acidified with glacial acetic and evaporated to give the product, compound 31, 4-amino-6-hydroxymethyl-2,5-dioxopyrido [2,3-d] pyrimidine. Compound 31 is recrystallized.

A solution of 1 mmole of compound 31 in anhydrous dimethylformamide, containing 2 mmole of anhydrous potassium carbonate and chloroacetic acid p-(methylthio) phenyl ester (1 mmole); prepared by DCC mediated condensation of chloroacetic acid with p-(methylthio) phenyl by standard procedures is added and the mixture is stirred overnight. The solvent is removed in vacuo and the residue is suspended in water, acidified, filtered and crystallized to yield the product compound 32, 4-amino-6-hyroxymethyl-2,5-dioxopyrido [2,3-d] pyrimidine-N$^8$-acetic acid p-methylthio) phenyl ester.

A solution of the sodium salt of methylthioacetic acid ethyl ester in tetrahydrofuran is prepared by the addition of sodium hydride to methylthioacetic acid ethyl ester. This solution is added to a solution of compound 32 in anhydrous dimethylformamide (DMF) and the solution is heated to 50° C. to 60° C. to complete the reaction. The progress of the reaction is monitored withdrawing samples, acidifying with acetic acid to quench the reaction, and observing the progress of the reaction by TLC. When the reaction is judged complete, the solution is acidified with acetic acid and the product is obtained by evaporation of the solvent followed by aqueous work-up to yield compound 33, 4-amino-6-hyroxymethyl-2,5-dioxopyrido [2,3-d] pyrimidine-y-(α-methylthio) acetic acid ethyl ester-N$^8$-acetic acid p-(methylthio) phenyl ester.

One mmole of compound 33 is briefly heated in ethanol with 1 gram (wet weight) of Raney Nickel to dethiate the 7-α-thiomethyl group. After the completion of the reaction, 1 mL of 1N HCl is added to the solution and the heating is continued to complete the lactonization. The product is obtained by evaporation of the solvents in vacuo, followed by crystallization, to yield the lactone derivative, which is compound 34. A suspension prepared with 1 mmole of the lactone derivative in 10 mL of anhydrous tetrahydrofuran and stirred with two equivalents of m-chloroperoxybenzoic acid for 3-5 hours. This reaction yields a mixture of sulfone and sulfoxide derivatives. The products are obtained by filtration.

EXAMPLE 14

Oligopeptides Comprising Side Chains for Intercalation of Doxorubicin

Experiments have been conducted to assess the use of synthetic oligopeptides to bind the drug doxorubicin. Binding was followed by changes in the visible spectrum of doxorubicin, and analyzed by titrating the drug absorption spectrum at 475 nm or 565 nm with varying concentrations of peptide, in pH 7.0 0.1M phosphate buffer. Binding curves were fit to a single hyperbola with the program Enzfitter (Elsevier-Biosoft). Results with oligopeptides used to screen for binding are shown in Table 2. These peptides were designed to test the effectiveness in intercalating doxorubicin of a 1,3-spacing between amino acids containing aromatic groups in their side chains (i.e., a single non-aromatic amino acid intervenes between the two residues having aromatic side chains). The amino acids are C, cys; K, lys; W, trp; G, gly; E, glu; D, asp; Fmoc, 9-fluorenylmethoxycarbonyl, attached to the lysine epsilon-amino group; and MIANS, 2-(4'-maleimidylanilino)naphthalene-6-sulfonic acid attached to cysteine.

The oligopeptides were synthesized using the boc-benzyl solid-phase peptide synthesis strategy of Barany and Merrifield as described in *The Peptides: Analysis, Synthesis, Biology*, E. Gross and J. Meienhofer (eds.), New York, Academic Press, 1980.

TABLE 2

Binding of Doxorubicin by Synthetic Oligopeptides

| Peptide | Peptide Sequence | Kd, μM |
|---|---|---|
| 1 | CKWGWK-amide | no detectable binding |
| 2 | CKWGWGWK-amide | same |
| 3 | CKWGWKWGWK-amide | same |
| 4 | KK(Fmoc)GK(Fmoc)KGGC | same |
| 5 | EK(Fmoc)GGK(Fmoc)EGGC | same |
| 6 | EK(Fmoc)K(Fmoc)EGGC | same |
| 7 | EK(Fmoc)GK(Fmoc)EGGC | 280 |
| 8 | DK(Fmoc)GK(Fmoc)DGGC | 22 |
| 9 | EK(Fmoc)EK(Fmoc)EGGC | no detectable binding |
| 10 | EEK(Fmoc)GK(Fmoc)EEGGC | 33 |
| 11 | EC(MIANS)GC(MIANS)EGGC(Acm) | 48 |

Figure 3A:
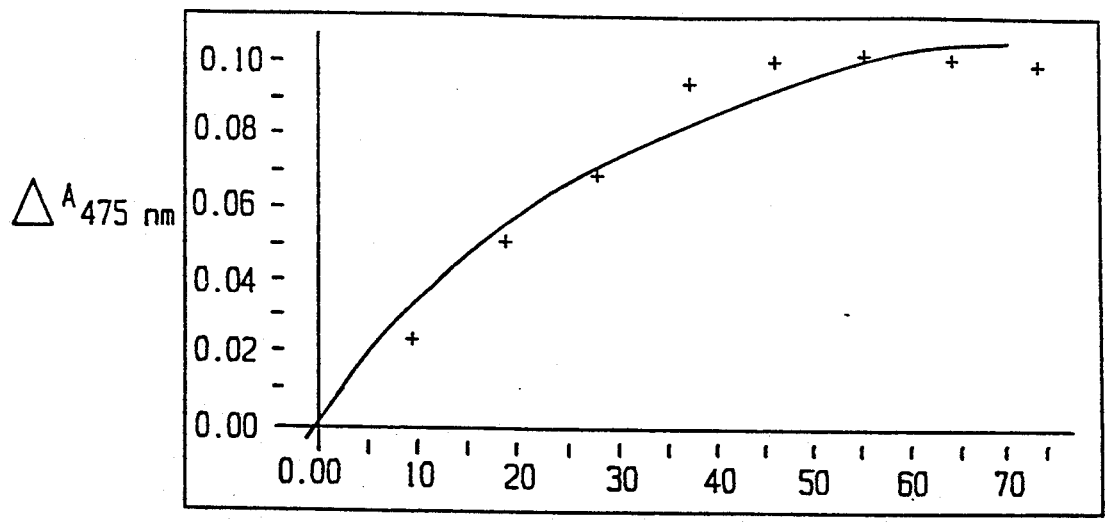

FIG. 3a is presented as an example of a titration curve resulting from these experiments, and shows the best-fit curve for titration of 50 μM doxorubicin with varying concentrations of the oligopeptide DK(Fmoc)GK(-Fmoc)DGGC-amide. No absorbance change was observed when the oligopeptide was added to buffer in the absence of doxorubicin. A concentration-dependent, saturable increase in absorbance occurs when oligopeptide is added to drug, suggesting formation of a complex between the two components. The oligopeptide carrier DK(Fmoc)GK(Fmoc)DGGC-amide was added in varying concentrations to doxorubicin (50 μM in 0.1M phosphate buffer at pH 7.0), and changes in the absorption spectrum of doxorubicin were observed at 475 nm. Oligopeptide carrier alone was added to the reference cuvette. The binding constant is derived from the nonlinear least squares best fit to a single hyperbola using the program Enzfitter (Elsevier-Biosoft), yielding an apparent dissociation constant of 22 μM.

Table 2 presents data on binding of doxorubicin by short peptides designed to test the binding ability of a peptide with 1,3 spacing of the aromatic side chains. In this series of peptides the binding units are WGW, C(MIANS)GC(MIANS), K(FMOC)GK(FMOC). When the 1,3 spacing is changed to 1,2 spacing (compare peptides 7 and 6) the apparent binding constant weakens from 280 μM to undetectable binding. When the spacing is changed to 1,4 spacing (peptide 7 vs. peptide 5) the same result is obtained.

The use of negatively charged residues flanking the putative binding unit also appears important. Peptides including lysines outside of this unit (peptides 1-4) show no detectable binding, while peptides with one or more negatively charged residues and a 1,3 spacing of an intercalating group (peptides 7-8, 10-11) bind doxorubicin. This may be due to ion pair formation between the positively charged amino group on the daunosamine moiety of doxorubicin and either glutamate or aspartate.

The central residue of the putative binding tripeptide also appears important. If this is glutamic acid (peptide 9) binding is not observed; if it is glycine, binding is seen (peptide 7). Substituting aspartate for glutamate (peptide 8) enhances binding, as does addition of additional negative charges (peptide 10). Thus, changing individual residues in the construction of new analogs can clearly improve binding.

Figure 3B:
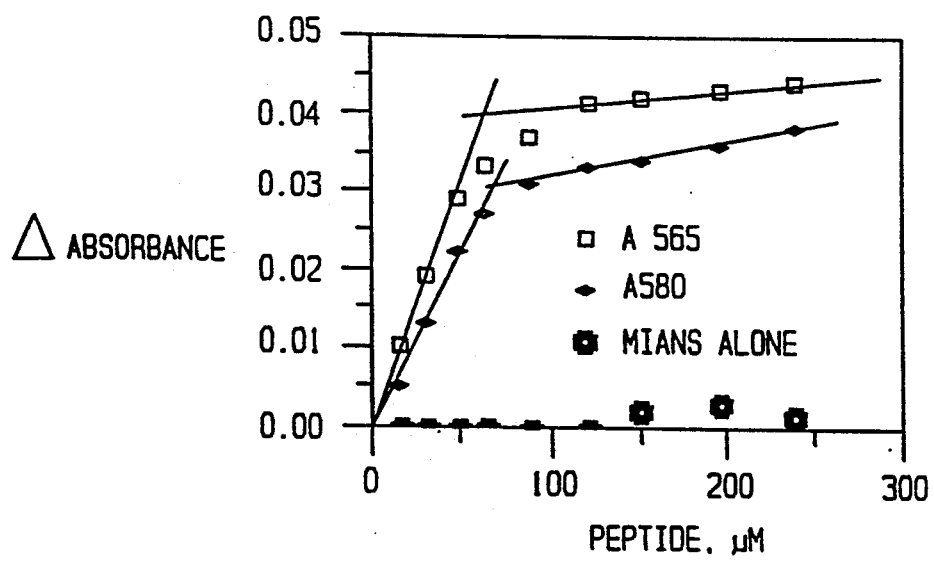

FIG. 3b shows the results for titration of doxorubicin with the oligopeptide EC(MIANS)GC(MIANS)EGGC(Acm). This oligopeptide was prepared by first synthesizing the oligopeptide ECGCEGGC(Acm), wherein "Acm" represents an acetamidomethyl protecting group. The synthesis was conducted using the solid phase methodology of Barany and Merrifield, supra, and Houghten, R. A., *Proc Nat. Acad. Sci. USA* 82:5131, 1985. The number of cysteine thiols per peptide was 1.8 as measured by titration with Ellman's reagent. See Means and Feeney, *Chemical Modification of Proteins*, San Francisco, Holden-Day, 1971, page 220.

The peptide concentration was determined with ninhydrin. (See H. Scheraga, *Pure Appl. Chem.* 50:315, 1978.) The oligopeptide then was alkylated with two moles of MIANS per mole of oligopeptide. MIANS (Molecular Probes, Eugene, Ore.) was derivatized to the two cysteine thiols of the peptide, and binding was followed as in FIG. 3a in pH 7.0 0.1M phosphate buffer, at 565 or 580 nm. The best-fit apparent dissociation constant was 48 μM.

These data suggest that aromatic side chains in a 1,3 spacing (as opposed to 1,2 or 1,4 spacing in this particular sequence) can help bind doxorubicin, and that binding of doxorubicin can be improved (about 6-fold) by use of a side chain (MIANS) which differs from FMOC.

From the foregoing, it will be appreciated that, although specific embodiments of the invention have been described herein for purposes of illustrations, various modifications may be made without deviating from the spirit and scope of the invention.

We claim:

1. A conjugate comprising an aromatic drug selected from anti-neoplastic anthracyclines and anthracycline derivatives, non-covalently intercalated between two aromatic side chains or an oligopeptide, and an antibody or antibody fragment covalently attached to the oligopeptide.

2. The conjugate of claim 1 wherein a non-aromatic amino acid is the only amino acid positioned between two amino acid residues having aromatic side chains in the oligopeptide.

3. The conjugate of claim 2 wherein the non-aromatic amino acid is glycine.

4. The conjugate of claim 3 wherein the oligopeptide contains at least one negatively charged amino acid selected from aspartic acid and glutamic acid.

5. A conjugate comprising doxorubicin non-covalently intercalated between two aromatic side chains on an oligopeptide, and an antibody or antibody fragment covalently attached to the oligopeptide.

6. The conjugate of claim 5 wherein the oligopeptide comprises a glycine residue positioned between two amino acid residues having aromatic side chains and the oligopeptide contains at least one negatively charged amino acid selected from aspartic acid and glutamic acid.

7. The conjugate of claim 6 wherein each of said aromatic side chains is a 9-fluorenyl-methoxycarbonyl side chain, which is attached to the epsilon amino group of a lysine residue.

8. The conjugate of claim 6 wherein each of said aromatic side chains is a 2-(4'-maleimidylanilino) naphthalene-6-sulfonic acid side chain, which is attached to the epsilon amino group of a lysine residue.

9. A conjugate comprising an aromatic drug selected from anti-neoplastic anthracyclines and anthracycline derivatives, non-covalently intercalated between two aromatic side chains on a synthetic oligopeptide, wherein said aromatic side chains are not naturally-occurring amino acid side chains, and an antibody or antibody fragment covalently attached to the oligopeptide.

10. The conjugate of claim 9 wherein glycine is the only amino acid positioned between two amino acids bearing said aromatic side chains in said synthetic oligopeptide.

11. The conjugate of claim 9 or 10 wherein said synthetic oligopeptide contains at least one negatively charged amino acid selected from aspartic acid and glutamic acid.

12. The conjugate of claim 9 wherein said aromatic drug is doxorubicin and said aromatic side chains are selected from 9-fluorenylmethoxycarbonyl side chains and 2-(4'-maleimidyl-anilino)naphthalene-6-sulfonic acid side chains.

* * * * *

UNITED STATES PATENT AND TRADEMARK OFFICE
CERTIFICATE OF CORRECTION

PATENT NO.  : 5,106,951
DATED       : April 21, 1992
INVENTOR(S) : Alton C. Morgan, Jr. et al.

It is certified that error appears in the above-identified patent and that said Letters Patent is hereby corrected as shown below:

In column 34, claim 1, line 36, please delete "or" and substitute therefor -- on --.

Signed and Sealed this

Thirteenth Day of July, 1993

Attest:

MICHAEL K. KIRK

Attesting Officer

Acting Commissioner of Patents and Trademarks